United States Patent
Hazen et al.

(12) 
(10) Patent No.: US 6,475,800 B1
(45) Date of Patent: Nov. 5, 2002

(54) INTRA-SERUM AND INTRA-GEL FOR MODELING HUMAN SKIN TISSUE

(75) Inventors: Kevin H. Hazen, Gilbert; James Matthew Welch, Tempe; Stephen F. Malin, Phoenix; Timothy L. Ruchti, Gilbert; Alexander D. Lorenz, Phoenix; Tamara L. Troy, Chandler; Suresh Thennadil, Tempe; Thomas B. Blank, Chandler, all of AZ (US)

(73) Assignee: Instrumentation Metrics, Inc., Chandler, AZ (US)

( * ) Notice: Subject to any disclaimer, the term of this patent is extended or adjusted under 35 U.S.C. 154(b) by 0 days.

(21) Appl. No.: 09/502,877

(22) Filed: Feb. 10, 2000

Related U.S. Application Data

(63) Continuation-in-part of application No. 09/359,191, filed on Jul. 22, 1999, now Pat. No. 6,280,381.

(51) Int. Cl.$^7$ ............................................. G01N 31/00
(52) U.S. Cl. ............................ 436/8; 436/71; 436/164; 436/166; 73/866.4; 252/408.1
(58) Field of Search ............................... 436/8, 63, 71, 436/164, 166; 73/866.4; 252/408.1; 600/309, 310, 316, 365

(56) References Cited

U.S. PATENT DOCUMENTS

| | | | |
|---|---|---|---|
| 4,266,877 A | | 5/1981 | Bodart .................. 356/414 |
| 4,277,367 A | | 7/1981 | Madsen et al. ............. 252/408 |
| 4,331,021 A | * | 5/1982 | Lopez et al. ................. 73/1.86 |
| 4,493,653 A | * | 1/1985 | Robbins et al. ............. 434/262 |
| 5,023,185 A | * | 6/1991 | Nambu et al. .................. 436/8 |
| 5,028,787 A | | 7/1991 | Rosenthal et al. .......... 250/341 |
| 5,066,859 A | | 11/1991 | Karkar et al. ................ 250/339 |
| 5,071,602 A | * | 12/1991 | Nambu et al. .................. 264/28 |
| 5,086,229 A | | 2/1992 | Rosenthal et al. .......... 250/341 |
| 5,250,262 A | | 10/1993 | Heidt et al. .................... 422/64 |
| 5,353,790 A | | 10/1994 | Jacques et al. ............. 128/633 |
| 5,451,528 A | | 9/1995 | Raymoure et al. .......... 436/533 |
| 5,514,670 A | * | 5/1996 | Friedman et al. ............... 514/2 |
| 5,523,054 A | | 6/1996 | Switalski et al. ............. 422/58 |
| 5,536,664 A | | 7/1996 | Switalski et al. ............. 436/171 |
| 5,607,565 A | | 3/1997 | Azarnia et al. ............. 204/403 |
| 5,625,137 A | * | 4/1997 | Madsen et al. .............. 73/1.84 |
| 5,635,364 A | | 6/1997 | Clark et al. ................ 435/7.92 |
| 5,657,754 A | | 8/1997 | Rosencwaig ................ 128/633 |
| 5,743,262 A | | 4/1998 | Lepper, Jr. et al. ......... 128/633 |
| 5,945,676 A | | 8/1999 | Khalil et al. ............ 250/339.12 |
| 6,011,626 A | | 1/2000 | Hielscher et al. ........... 356/367 |
| 6,190,915 B1 | * | 2/2001 | Madsen et al. .................. 436/8 |

FOREIGN PATENT DOCUMENTS

| | | |
|---|---|---|
| DE | 4316326 | 6/1964 |
| EP | 0757243 | 2/1997 |
| EP | 0988857 | 3/2000 |
| WO | WO 98/37869 | 9/1998 |
| WO | WO 99/09395 | 2/1999 |

OTHER PUBLICATIONS

Allardice, J., A. Abulafi, D. Webb, and N. Williams. "Standardization of Intralipid for Light Scattering in Clinical Photodynamic Therapy," *Lasers in Medical Science*, 1992.

Arnold, M., J. Burmeister, G. Small. "Phantom Glucose Calibration Models from Simulated Noninvasive Human Near–Infrared Spectra," *Analytical Chemistry*, vol. 70, No. 9, May 1, 1998.

Chance, B., H. Liu, T. Kitai, and Y. Zhang. "Effects of Solutes on Optical Properties of Biological Materials: Models, Cells, and Tissues," *Analytical Biochemistry*, vol. 227, 1995.

Driver, I., J.W. Feather, P.R. King and J.B. Dawson. "The optical properties of aqueous suspensions of Intralipid, a fat emulsion," *Physical Medicine Biology*, vol. 34, No. 12, 1989.

Du, C., W. Nahm, H. Gehring, and E. Konecny. "Quantification of NIRS data of a blood phantom by spectral multi-component analysis," *SPIE*, vol. 2626, Date Unknown.

Eber, R., B. Parthey, and J. Wilke. "A Sensor for Investigations of the complex refractive Index of Liquids in the NIR range," *Fachbereich Lebensmittel–und Biotechnologie*, 1983.

F. Henn and T.E. Thompson, "Synthetic Lipid Bilayer Membranes," *Department of Biochemistry*, Virginia, 1969.

(List continued on next page.)

Primary Examiner—Maureen M. Wallenhorst
(74) Attorney, Agent, or Firm—Michael A. Glenn; Christopher Peil

(57) ABSTRACT

The invention provides a class of samples that model the human body. This family of samples is based upon emulsions of oil in water with lecithin acting as the emulsifier. These solutions that have varying particle sizes may be spiked with basis set components (albumin, urea and glucose) to simulate skin tissues further. The family of samples is such that other organic compounds such as collagen, elastin, globulin and bilirubin may be added, as can salts such as $Na^+$, $K^+$ and $Cl^-$. Layers of varying thickness with known index of refraction and particle size distributions may be generated using simple crosslinking reagents, such as collagen (gelatin). The resulting samples are flexible in each analyte's concentration and match the skin layers of the body in terms of the samples reduced scattering and absorption coefficients, $\mu m_s$ and $\mu m_a$. This family of samples is provided for use in the medical field where lasers and spectroscopy based analyzers are used in treatment of the body. In particular, knowledge may be gained on net analyte signal, photon depth of penetration, photon radial diffusion, photon interaction between tissue layers, photon density (all as a function of frequency) and on instrument parameter specifications such as resolution and required dynamic range (A/D bits required). In particular, applications to delineate such parameters have been developed for the application of noninvasive glucose determination in the near-IR region from 700 to 2500 nm with an emphasis on the region 1000 to 2500 nm (10,000 to 4,000 $cm^{-1}$).

15 Claims, 21 Drawing Sheets

OTHER PUBLICATIONS

Flock, S., S. Jacques, B. Wilson, W. Star, and M. van Gemert. "Optical Properties of Intralipid: A Phantom Medium for Light Propagation Studies," *Lasers in Surgery and Medicine*, 1992.

Freiherr, Greg. "The Light Stuff: Optical Imaging in Medical Diagnosis," *Medical Device and Diagnostic Industry*, Jun. 199.

Hielscher, A., J. Mourant, and I. Bigio. "Influence of particle size and concentration on the diffuse backscattering of polarized light from tissue phantoms and biological cell suspensions,"*Applied Optics*, vol. 36, No. 1, Jan. 1997.

Introduction to Biological Membranes, Chapter 12, Date Unknown.

M. Kohl and M. Cope. "Influence of glucose concentration on light scattering in tissue–simlating phantoms," *Optical Society of America*, vol. 19, No. 24, Dec. 1994.

Madsen, S., M. Patterson and B. Wilson. "The use of India ink as an optical absorber in tissue–simulating phantoms," *Physical Medical Biology*vol. 37, No. 4, 1992.

Maier, J., S. Walker, S. Fantini, M. Franceschini, and E. Gratton. "Possible Correlation between blood glucose concentration and the reduced scattering coefficient of tissues in the near infrared," *Optical Society of America*, vol. 19, No. 24, Dec. 15, 1994.

McCord, T.B., G.B. Hansen, F.P. Fanale, R.W. Carlson, D.L. Matson, T.V. Johnson, W.D. Smythe, J.K. Crowley, P.D. Martin, A. Ocampo, C.A. Hibbitts, J.C.Granahan, and the NIMS Team. "Salts on Europa's Surface Detected by Galileo's Near Infrared Mapping Spectrometer," *Science*, Vol. 280, May 22, 1998.

Moes, C., M. van Gernert, W. Star, J. Marijnissen, and S. Prahl. "Measurements and calibrations of the energy fluence rate in a scattering and absorbing phantom at 633 nm," *Applied Optics*, vol. 28, No. 12, Jun. 15, 1989.

Mourant, J., T. Fuselier, J. Boyer, T.M. Johnson, and I. Bigio. "Predictions and Measurements of scattering and absorption over broad wavelength ranges in tissue phantoms," *Applied Optics*, vol. 36, No. 4, Feb. 1997.

Parsa, P., S. Jacques, and N. Nishioka. "Optical Properties of Rat Liver Between 350 and 2200nm," *Applied Optics*, vol. 28, No. 12, Jun. 15, 1989.

Schmitt, J.M. G.X. Zhou, and E.C. Walker. "Multilayer model of photon diffusion in skin," *Optical Society of America*, vol. 7, No. 11, Nov. 1990.

U. Sathyam and S. Prahl. "Limitations in Measurement of Substance Temperatures Using Pulsed Photothermal Radiometry," *Journal of Biomedical Optics*, vol. 2, No. 3, Jul. 1997.

Van Gemert, M.J.C., S. Jacques, H.J.C.M. Sterenborg, and W.M. Star. "Skin Optics," *IEEE*, vol. 36, No. 12, Dec. 1989.

Van Staveren, H., C. Moes, J. van Marle, S. Prahl, and M. van Gemert. "Light Scattering in Intralipid–10% in the wavelength range of 400–1100 nm,"*Applied Optics*, vol. 30, No. 31, Nov. 1991.

Waterworth, M., B. Tarte, A. Joblin, T. van Doorn, and H. Niesler. "Optical Transmission Properties of Homogenised Milk Used as a Phantom Material in Visible Wavelength Imaging," *Australasian Physical & Engineering Sciences in Medicine*, vol. 18, No. 1, 1995.

Y.A. Carpentier. "Intravascular Metabolism of Fat Emulsions: The Arvid Wretlind Lecture, Espen 1988," *Clinical Nutrition*, 1989.

\* cited by examiner

Distrubution of Particle Sizes in Castor Oil Intralipid $\mu_a$ vs. Wavelength for 3% Castor Oil Intralipid as compared to the water curve Intra-Serum Components, Transmission Spectra ----- Urea
--- Albumin
— Glucose Comparison of Arm and Castor Oil Intralipid

INTRA-SERUM AND INTRA-GEL FOR MODELING HUMAN SKIN TISSUE

CROSS-REFERENCE TO RELATED APPLICATION

This application is a Continuation-in part of U.S. patent application Ser. No. 09/359,191, filed on Jul. 22, 1999, now U.S. Pat. No. 6,280,381, issued on Aug. 28, 2001.

BACKGROUND OF THE INVENTION

1. Technical Field

The invention relates to noninvasive spectroscopy. More particularly, the invention relates to the modeling of human tissue for use in noninvasive spectroscopy.

2. Description of the Prior Art

In the field of noninvasive spectroscopy, photons generated by a source penetrate into the body of a subject, interact with the subject's tissue layers and exit to a detector. The interaction with the tissue layers is complex and is not well understood. Models that simulate the tissue may be utilized to address such fundamental questions as the net analyte signal, depth of penetration of the photons and radial diffusion of the photons. Knowledge of the exact chemical composition of a tissue surrogate will allow chemical and physical interpretation of spectra obtained on human skin where the exact chemical composition of the sample is unknown. For these reasons, a model of skin tissue samples would be beneficial.

SUMMARY OF THE INVENTION

The invention provides a class of samples that model the human body. This family of samples is based upon emulsions of oil in water with emulsifiers such as lecithin used to keep the solution from separating. These emulsions have oil droplets with varying particle sizes acting as scatterers and may be spiked with basis set components (e.g. albumin, globulin, urea and glucose) to simulate skin tissues further. The family of samples is such that other organic compounds, such as collagen, elastin, globulin, lactic acid and bilirubin may be added, as can salts such as $Na^+$, $K^+$ and $Cl^-$. Layers of varying thickness with known index of refraction and particle size distributions may be generated using simple crosslinking reagents, such as collagen. The resulting samples are flexible in that each analyte's concentration may be adjusted independently of the others and that each skin layer of the body may be matched in terms of the samples' reduced scattering and absorption coefficients, $\mu'_s$ and $\mu_a$.

Physiological glucose concentrations are determined in diffuse reflectance mode using near-IR spectroscopy on novel tissue-simulating phantoms. The tissue phantom, which is composed of water and a modified Intralipid solution is similar to skin of the human forearm in terms of its absorption and reduced scattering coefficients. Albumin and urea are added to the samples acting as additional interferences present in the body and as diluents allowing experimental designs that ensures that the glucose concentration is not correlated with time, additional matrix constituents or reference spectra. All major near-IR absorbers of skin tissue in the 1100 to 2500 nm region are present in the resulting tissue phantom. Using reference spectra to model instrumentation drift, an f-test demonstrates that multivariate analyses are not modeling correlations between glucose concentrations and spectrometer variations. Glucose determinations are demonstrated independently in the $2^{nd}$ overtone region, $1^{st}$ overtone region and combination band region with SEP's of 40.0, 13.5 and 29.6 mg/dL, respectively. This work demonstrates the feasibility of diffuse reflectance near-IR determination of glucose in the body.

This family of samples is provided for use in the medical field where lasers, laser diodes, LED's and spectroscopy based analyzers are used in the treatment of the body. In particular, knowledge may be gained on photon depth of penetration, photon radial diffusion, photon interaction between tissue layers, photon density (all as a function of frequency), and on instrument parameter specifications, such as resolution and required dynamic range (i.e. A/D bits required). In particular, applications to delineate said parameters have been developed for the application of noninvasive glucose determination in the near-IR region from 700 to 2500 nm with an emphasis on the region from 1000 to 2500 nm (10,000 to 4000 $cm^{-1}$).

DETAILED DESCRIPTION OF THE INVENTION

Figure 1:
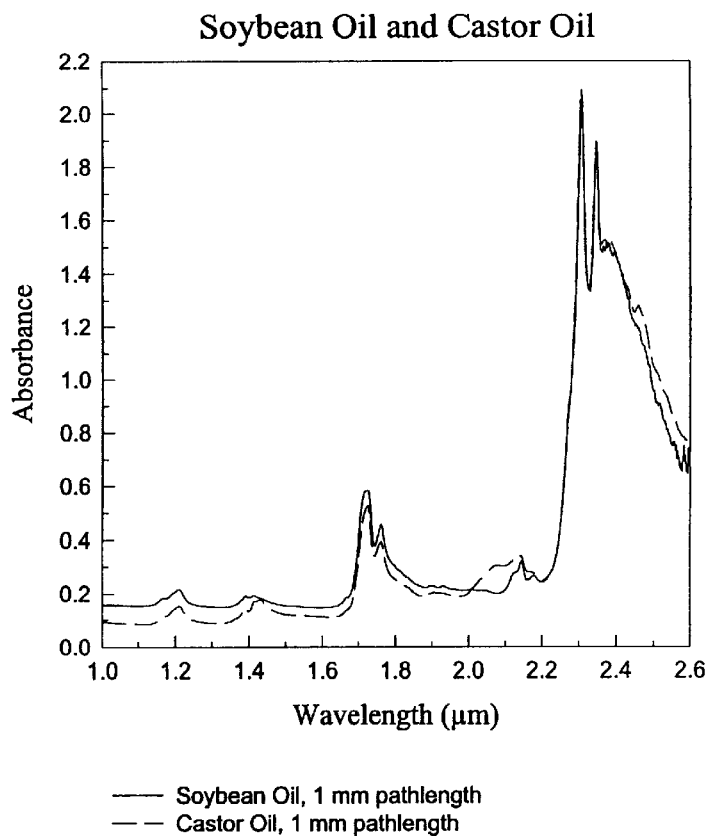
FIG. 1 shows absorbance spectra of 100% soybean oil and castor oil.

Many academic and industrial groups continue to work towards the realization of a noninvasive glucose meter based upon near-IR radiation. Several reports exist where glucose is measured noninvasively in transmittance mode (see Hazen, Kevin H. *Glucose Determination in Biological Matrices Using Near-Infrared Spectroscopy*, Ph.D. Dissertation, University of Iowa (1995); and Burmeister, Jason Joe, Ph.D. Dissertation, *In Vitro Model for Human Noninvasive Blood Glucose Measurements* University of Iowa, (1997); and Robinson, Ries M., Eaton, Philip R., Haaland, David M., Koepp, Gary W., Thomas, Edward V., Stallard, Brian R., Robinson, Paul L. Clinical Chemistry, vol. 38, pp.1618–1622 (1992)). Interpretation of these reports is complicated by the fact that there are several large interferences present that spectrally overlap the glucose and that the body is a dynamic system. A series of transmission based studies have broken down this complex problem into controlled studies where individual affects such as the interference of water, protein, and urea are addressed as are environmental issues such as temperature (see M. Arnold, G. Small, *Analytical Chemistry*, vol. 62, pp. 1457–1464 (1990); L. Marquardt, M. Arnold, *Analytical Chemistry*, vol. 65, pp. 3271–3278 (1993); and K. Hazen, M. Arnold G. Small, *Applied Spectroscopy*, vol. 48, pp. 477–482 (1994)). These interferences have been combined into complex matrices demonstrating feasibility of glucose determinations in the presence of all serum components and in blood (see K. Hazen, M. Arnold, G. Small, *Analytica Chimica Acta*, vol. 371, pp.255–267 (1998). This work has been expanded to include instrumentation issues such as wavelength selection or resolution (see Q. Ding, G. Small, M. Arnold, *Analytical Chemistry*, vol. 70, pp. 4472–4479 (1998)). All of this work has been analyzed using a series of chemometric approaches (see R. Shaffer, G. Small, M. Arnold, *International Journal of Computer Vision*, vol. 18, pp. 2663–2675 (1996)). While this work has led to considerable insights in near-IR based glucose measurements in both transmission and diffuse reflectance based spectroscopy, several parameters related to the diffuse reflectance measurement would be better answered if these variables were addressed in a diffuse reflectance medium.

Noninvasive determinations of glucose in the near-IR using diffuse reflectance spectroscopy have been reported (H. Heise, R. Marbach, Th. Koschinsky, F. Gries, *Artificial Organs*, vol. 18, pp. 439–447 (1994); and S. Malin, T. Ruchti, T. Blank, S. Thennadil, S. Monfre, *Clinical Chemistry*, vol. 45, pp. 1651–1658 (1999); and K. Jagemann, C. Fishbacher, K. Danzer, U. Muller, B. Mertes, *Zeitschrift fur Physikalische Chemie*, vol. 191s, pp. 179–190 (1995)). Existing transmission studies lead to difficulties in deducing such fundamental concerns in diffuse reflectance studies as depth of penetration of photons, total optical pathlength, photon distribution as a function of depth and changes in the scattering coefficient with depth. In addition, some instrument parameters such as resolution and required dynamic range will differ for a diffuse reflectance based glucose analyzer. Therefore, studies must be completed in a diffuse reflectance medium that are equivalent to the body of work addressing interferences, instrumentation parameters and chemometric approaches performed in transmission mode.

A suitable diffuse reflectance medium needs to be generated that allows these studies to be performed. Several design criteria exist for the tissue phantom. First, the absorbance and reduced scattering coefficients of the tissue phantom should approximate that of human skin in the 1000 to 2500 nm spectral region. Second, constituents of the tissue phantom should represent all major near-IR interferences of glucose in the skin. Third, interferences should not be introduced into the tissue phantom that are not present in the skin. Fourth, a family of samples needs to be created in which the concentrations of all individual components of the sample are quantitatively known and that they may be analytically varied such that, within a study, each analyte may be random in concentration versus the other analytes. Finally, the exact chemical and physical makeup of the sample needs to be known.

It will be demonstrated in this paper that modifications to commercial Intralipid create a base scattering solution upon which a tissue phantom may be created that models the human body. This family of samples is based upon emulsions of oil in water with lecithin acting as the emulsifier. These solutions with varying particle sizes may be spiked with albumin, urea and glucose to further simulate skin tissues. The family of samples is such that other organic compounds such as collagen, elastin, globulin, lactic acid and bilirubin may be added, as can salts such as $Na^+$, $K^+$ and $Cl^-$. Collectively, the resulting family of samples is known as Intra-serum. Layers of varying thickness with known index of refraction and particle size distributions may be generated using simple crosslinking reagents, such as collagen. The resulting samples are flexible in the concentration of each analyte and match the skin layers of the body in terms of the samples reduced scattering and absorption coefficients, $\mu'_s$ and $\mu_a$. The resulting sample may also be shaped to match the curvature of the skin, for example the forearm.

Intralipid Properties

Commercial Intralipid is a fat emulsion used clinically as an intravenous nutrient and is manufactured by Kabivitrum (Stockholm, Sweden) and by Fresenius Kabi (West Clayton, N.C.). Three forms of Intralipid are manufactured: 10, 20 and 30%, which refers to the soybean oil concentration. Commercial Intralipid is made up of water, soybean oil, glycerol and lecithin. Table 1 shows the composition of 10, 20 and 30% Intralipid (see J. Allardice, M. Abulafi, D. Webb, N. Williams, *Lasers in Medical Science*, vol. 7, pp. 461–465 (1992)). From the tabulated data, it should be noted that the ratio of the soybean oil to the other constituents is not fixed indicating that literature values need to be interpreted based upon the stock Intralipid solution referenced.

TABLE 1

Constituents of 10, 20 and 30% Intralipid.

| Component | 10% Intralipid (g/L) | 20% Intralipid (g/L) | 30% Intralipid (g/L) |
| --- | --- | --- | --- |
| Fractionated Soybean Oil | 100 | 200 | 300 |
| Fractionated Egg Phospholipids | 12 | 12 | 12 |
| Glycerol | 22.5 | 22.5 | 22.5 |

In Intralipid, small soybean oil droplets are emulsified by a lecithin monolayer to form scatterers. Utilizing a Coulter Counter, the mean size of the particles in Intralipid-10% is 1.00 µm with a standard deviation of 0.14 µm (see C. Moes, M. van Gemert, W. Star, J. Marijnissen, S. Prahl, *Applied Optics*, vol. 28, pp. 2292–2296 (1989)). Freeze fracture studies have yielded a mean particle size of 97.3 nm, excluding those below 20 nm, by transmission electron microscopy with an exponential decrease in probability with increasing size reaching zero for a 700 nm diameter (see H. van Staveren, C. Moes, J. van Marie, S. Prahl, M. van Gemert, *Applied Optics*, vol. 30, pp. 4507–4514 (1991)). These particles sizes indicate that 60 to 90% of the Intralipid soybean droplets are small enough to act as Rayleigh scatterers at the frequencies of interest from 1100 to 2500 nm. Emulsified particles are spherical with a form factor of 0.97 with an ideal sphere having a value of 1. Form factors above 0.80 will not significantly influence Mie scattering calculations. This implies that the very slight nonspherical nature of the particles will not effect Mie scattering calculations (see H. van Staveren, C. Moes, J. van Marie, S. Prahl, M. van Gemert, *Applied Optics*, vol. 30, pp. 4507–4514 (1991)).

The reduced scattering coefficient $\mu'_s$, absorption coefficient $\mu_a$ and anisotropy coefficient g of Intralipid have been determined in the visible and short wavelength (700 to 1000 nm) region of the near-IR (see S. Flock, S. Jacques, B. Wilson, W. Star, M. van Gemert, *Lasers in Surgery and Medicine*, vol. 12, pp. 510–519 (1992); and H. van Staveren, C. Moes, J. van Marie, S. Prahl, M. van Gemert, *Applied Optics*, vol. 30, pp. 4507–4514 (1991)). Inconsistencies in optical parameters have been blamed on inconsistencies in the manufacturing process of the commercial Intralipid (see S. Flock, S. Jacques, B. Wilson, W. Star, M. van Gemert, *Lasers in Surgery and Medicine*, vol.12, pp. 510–519 (1992); and H. van Staveren, C. Moes, J. van Marie, S. Prahl, M. van Gemert, *Applied Optics*, vol. 30, pp. 4507–4514 (1991)). Generally, the total attenuation coefficient and absorption coefficient decrease as wavelength increases from 450 to 700 nm. Scattering dominates absorbance by a factor of 13,400 times at 633 nm. The anisotropy coefficient shows scatter to be primarily in the forward direction falling from 0.88 to 0.72 from 450 to 1100 nm. Values for these coefficients from 1100 to 2500 nm are reported later in this work. At these longer wavelengths, the absorption coefficient will no longer be dominated by the scattering coefficient and will have to be explicitly added to the models used to generate these coefficients.

Due to its light scattering properties, Intralipid has been employed as a part of a tissue phantom in the visible and short wavelength near-IR regions. Commercially available Intralipid solutions are found to be unacceptable for such uses as, for example, glucose studies, due to strong glycerol absorbance bands that are highly correlated with glucose absorbance bands.

Intralipid Component Spectra

As discussed above, commercial Intralipid is a fat emulsion composed of water, soybean oil, lecithin and glycerol. In this section, spectral characteristics of each component are identified.

The major component of Intralipid is water. Near-IR absorbance of water has been well characterized and has strong absorbance bands at 1450, 1900 and 2600 nm (see K. Hazen, *Glucose Determination in Biological Matrices Using Near-infrared Spectroscopy*, Ph.D. Dissertation, University of Iowa (1995)). As water makes up approximately 70% of skin tissue, inclusion of water in a matrix simulating the body is beneficial.

Figure 2:
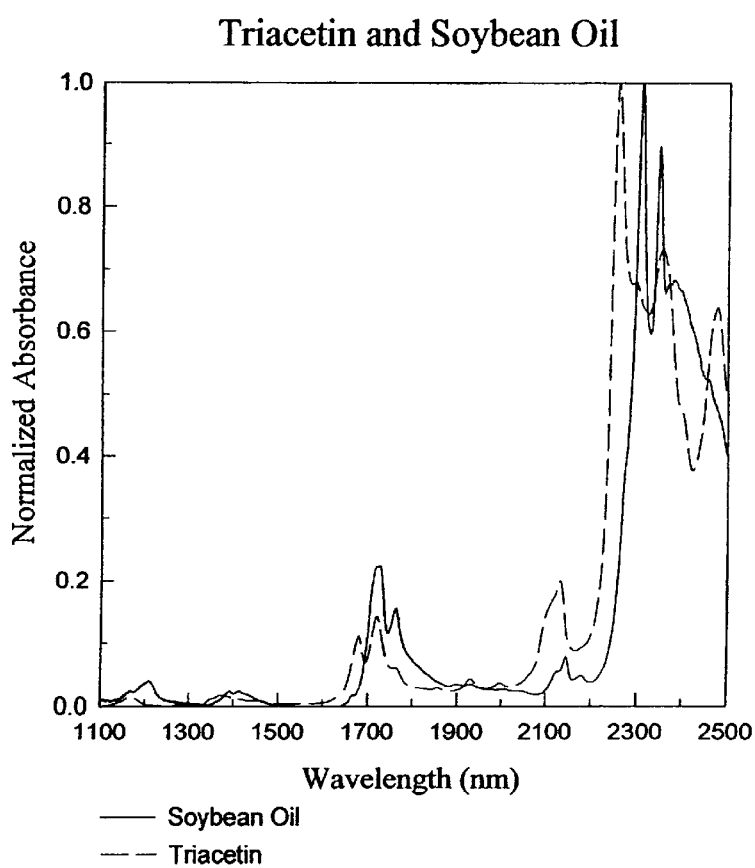
FIG. 2 shows absorbance bands at 1167, 1210, 1391, 1413, 1724, 1760, 2123, 2144, 2307, 2347 and 2380 nm for soybean oil which are red shifted versus triacetin absorbance bands, which have been used to simulate fat.

A second constituent of Intralipid is oil in the form of droplets that make up the primary scattering components. Commercial Intralipid is made up of soybean oil, which has absorbance bands at 1167, 1210, 1391, 1413, 1724, 1760, 2123, 2144, 2307, 2347 and 2380 nm, FIG. 1. Notably, the long chain oil yields absorbance bands that are red shifted versus the short carbon chain triacetin absorbance bands which for solubility reasons have been used to simulate fat in earlier serum phantoms, FIG. 2. Pork fat, after removing the water component, shows absorbance bands that match the long chain oils. Soybean oil is made up of linoleic (44–62%), oleic (19–30%), palmitic (7–14%), linolenic (4–11%) and stearic acids (1.4–5.5%) which simulate well the long chain saturated and unsaturated fatty acid chains found in cell membranes and fat deposits within the body (see Documentation provided with Intralipid-10%, Clintec Nutrition Division of Baxter Healthcare Corporation). Every soybean oil band observed corresponds to a fat absorbance band in skin with the exception of the two absorbance bands at 1400 nm which are obscured by water. For these reasons, the soybean oil element of Intralipid is beneficial in a tissue phantom.

Figure 3:
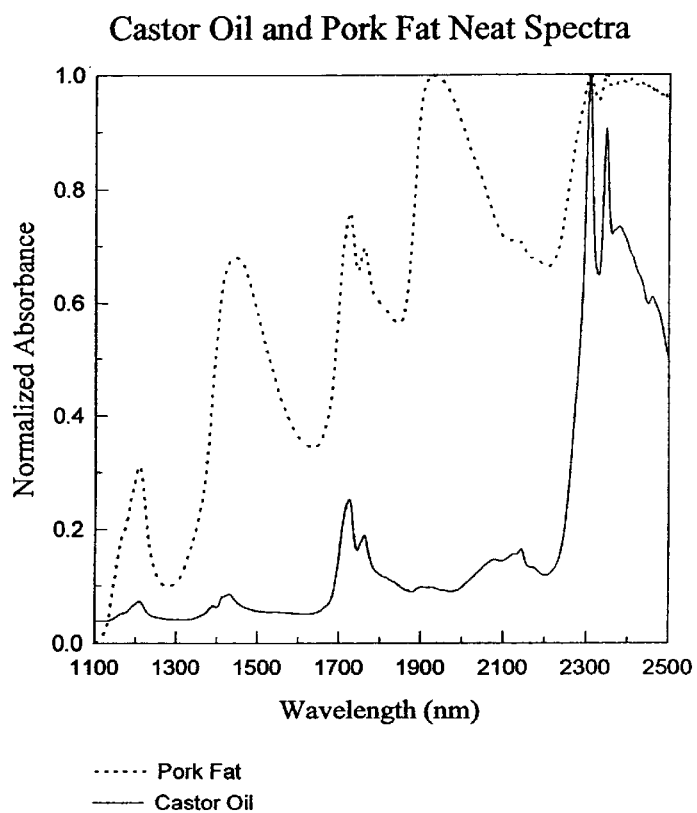
FIG. 3 shows fat absorbance bands in similar locations for normalized absorbance spectra of 100% castor oil and pork fat.

Castor oil has the same absorbance bands as soybean oil, but due to its viscosity is the preferred oil in the Intra-serum samples as it is better able to form larger droplets in solution. Castor oil is made up of ricinoleic (87%), oleic (7%), linoleic (3%), palmitic (2%) and stearic (1%) acids (see *Merck Index* 12$^{th}$ *Edition,* Merck and Co., Inc., pp. 311–312 (1996)). The primary component of castor oil is ricinoleic acid, which is a $C_{18}$ fatty acid chain. The long chain saturated and unsaturated fatty acid chains are found in cell membranes and fat deposits within the body. The strong absorbance band at 2256 nm in triacetin has been demonstrated to be due to the three-carbon backbone of triglycerides rather than the long chain fatty acids, data not presented. Further, after the removal of the water band at 1450 and 1950 nm, FIG. 3 shows that every castor oil band observed corresponds to an adipose tissue band with the exception of the two absorbance bands at 1400 nm which are obscured by water. In addition, three of the castor oil absorbance bands at 1210, 1720 and 1760 nm are readily identified in noninvasive spectra. For these reasons, the castor oil element of Intralipid is viewed as a natural component of the body and is viewed as a desirable absorbing element of Intra-serum. The concentration of this oil is held constant in initial studies presented here and varied in subsequent studies to simulate the variation of this component in the epidermal and dermal layers of skin.

In the modified Intralipid solution, the oil is coated with lecithin, a phosphatidylcholine. Lecithin is insoluble in water but swells up in water and sodium chloride solutions to form a colloidal suspension. Lecithin has a density of 1.0305 at 24° C. It is commonly used as a digestible surfactant and emulsifier of natural origin (see The Merck Index Eighth Edition, Merck & Co., Inc. Rahway, N.J., pp. 615 (1968)). The zwitterion nature of the choline ester allows lecithin to act as an emulsifier forming a monolayer around small oil particles resulting in near-IR scatterers. Fat emulsions made of soybean oil and emulsified by egg phosphatides are exclusively composed of long-chain triglycerides (see Y. Carpentier, *Clinical Nutrition,* vol. 8, pp.115–125 (1989)).

Figure 4:
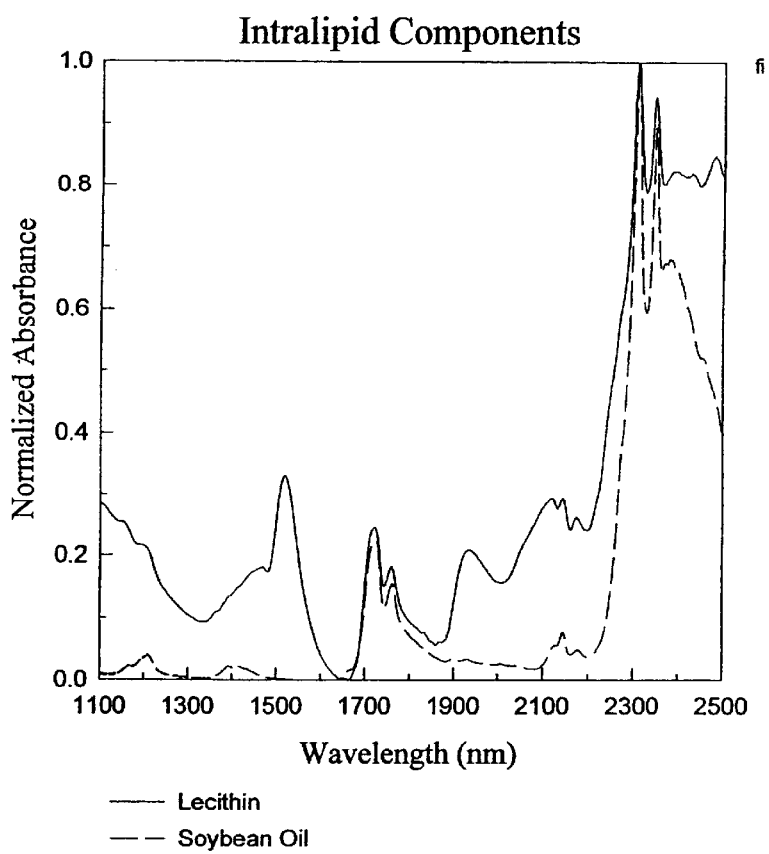
FIG. 4 shows normalized absorbance spectra of lecithin run as a pressed pellet of 10% lecithin/90% $K^+Br^-$ and soybean oil.

An absorbance spectrum of lecithin collected as a 10% lecithin, 90% KBr crushed pellet in transmission mode demonstrates that the primary absorbance bands of lecithin match those of soybean oil, FIG. 4. This is expected since lecithin is a mixture of the diglycerides of stearic, palmitic and oleic acids which are the primary constituents of soybean oil. Additional absorbance bands observed at 1518 and 1938 may be due to the choline ester.

The observed absorbance of lecithin in solution increases from 1300 to 1100 nm due to scattering of light. In lntralipid-10% approximately half of the lecithin is used to coat soybean oil droplets (see H. van Staveren, C. Moes, J. van Marie, S. Prahl, M. van Gemert, *Applied Optics,* vol. 30, pp. 4507–4514 (1991)). Centrifugation studies show that one-third of the lecithin is used to coat the oil in lntralipid-10% and ⅔ is used to coat the oil in lntralipid-20% (see Y. Carpentier, *Clinical Nutrition,* vol. 8, pp. 115–125 (1989)). These later numbers support the total amount of lecithin being used in the lntralipid-30%. Excess lecithin forms small bilayer vesicles. Since lecithin has two fatty acid acyl chains, steric effects prevent the formation of micelles (see L. Stryer, *Biochemistry* 3$^{rd}$ *Edition,* W.H. Freeman and Company (1988)). Therefore, the excess insoluble lecithin will swell to form a colloidal suspension of small bilayer vesicles that scatter light. The internal compartment of the vesicle is a water phase separated by a lipid bilayer from another water phase. Lecithin is a mixture of diglycerides of stearic, palmitic, and oleic acids linked to the choline ester of phosphoric acid and is found in all living organisms. Lecithin which creates scattering droplets with oil, is naturally occurring in all living organisms and has absorbance bands in the same location as body fat is considered a good element of a tissue phantom.

Figure 5:
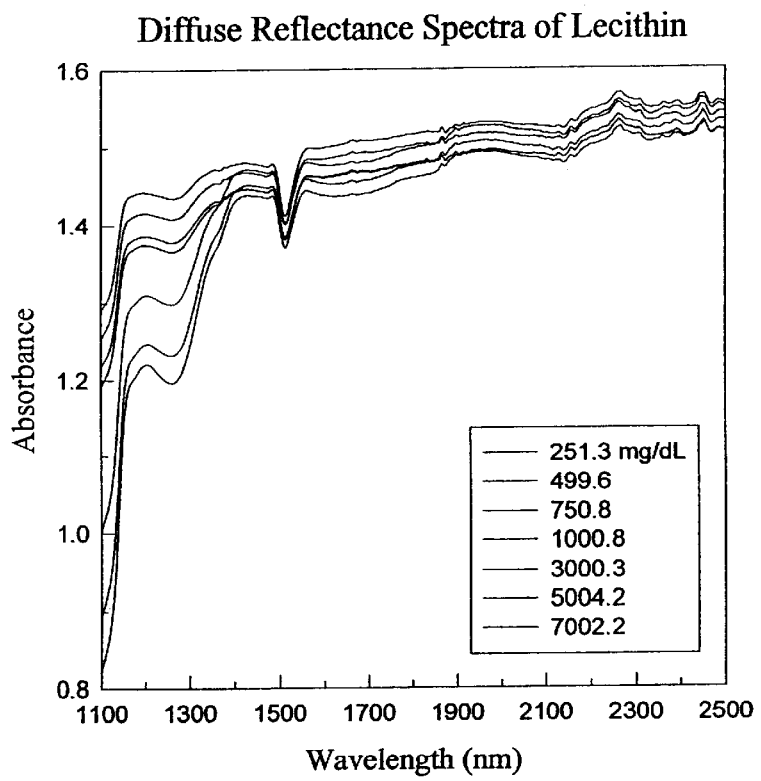
FIG. 5 shows diffuse reflectance spectra of lecithin in deionized $H_2O$ prepared with concentrations varying from 250 to 7000 mg/dL in an infinite pathlength cell.

Lecithin in deionized water was prepared with concentrations varying from 250 to 7000 mg/dL. Diffuse reflectance spectra of these samples were collected on an NIRS 5000 with an infinite pathlength cell and are presented in FIG. 5. The feature at 1500 nm is Wood's anomaly. From 1100 to 1400 nm it is observed that, as the lecithin concentration increases, the absorbance decreases. This is consistent with an increase in a scattering element. Additional lecithin results in additional lipid bilayer vesicles, which are scatterers. Additional scatterers results in a shorter average pathlength before the photons return to the incident plane. This shorter pathlength results in less absorbance from water. From 1500 to 2500 nm additional questions arise as to the cause of the decrease in absorbance with increasing lecithin concentration. The difference may be due to the displacement of water and/or the difference may result from a refractive index change. As the lecithin concentration increases, more light is reflected. This figure presents strong evidence that additional lecithin in solution that forms lipid bilayer vesicles results in additional scatterers.

Figure 6:
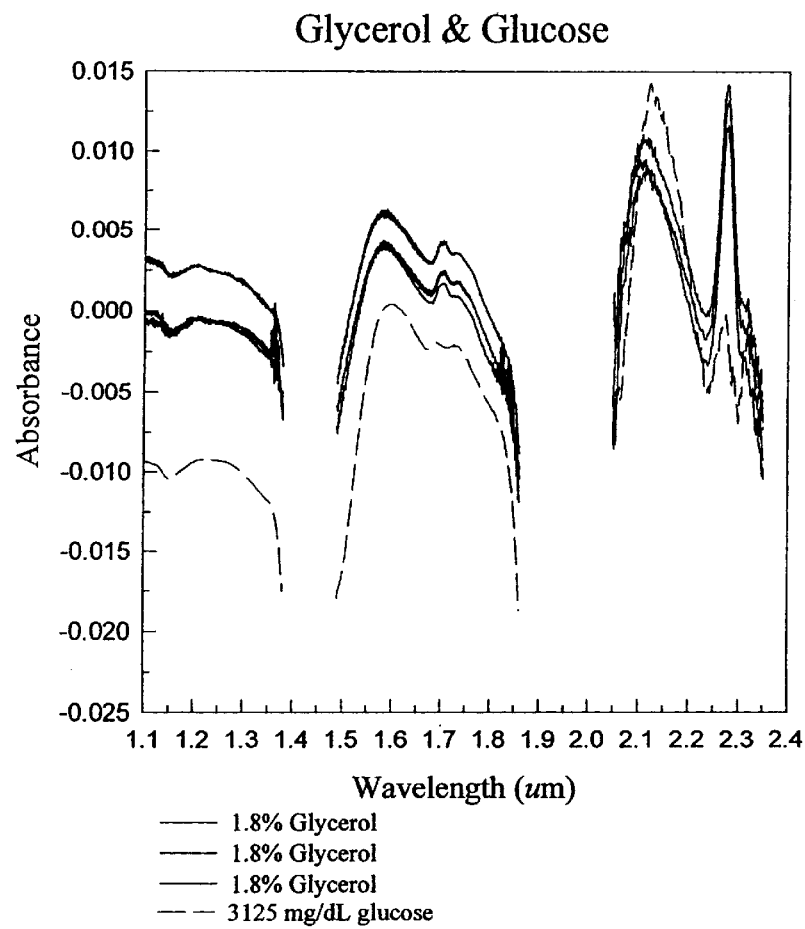
FIG. 6 shows absorbance spectra of 1.8% glycerol and 3125 mg/dL glucose.

The final component of commercial Intralipid is glycerol ($C_3H_8O_3$), also known as glycerin or 1,2,3-propanetriol. Glycerol is miscible with water and has an index of refraction of 1.4730 (see The Merck Index Eighth Edition, Merck & Co., Inc. Rahway, N.J., pp. 499 (1968). While glycerol will not form particles of scattering dimensions in the near-IR region the density and index of refraction difference from the aqueous phase will lead to small changes in scattering. Glycerol contributes insignificantly to the overall absorbance of Intralipid compared to water, soybean oil and lecithin. Glycerol has a concentration in Intralipid of 1.8%. Absorbance spectra of 1.8% glycerol with a 0.5 and 1.0 mm pathlength collected in transmittance mode with an air background are presented in FIG. 6. Overlaid on this figure is an absorbance spectrum of 3125 mg/dL glucose using water as a reference. Glycerol has absorbance bands at 1626, 1689, 1732, 2105, 2272 and 2326 nm, all of which correlate with glucose absorbance bands. Glucose at a concentration of approximately 3000 mg/dL has absorbance bands that correspond in position and magnitude to 1.8% glycerol. Near-IR analysis of glucose with diabetic physiological ranges of 30–700 mg/dL in the presence of varying amounts of glycerol using standard chemometric techniques would be very difficult. Finally, glycerol, which is present in the body, is not a major constituent of skin or blood. For these reasons, glycerol is not a preferable constituent of a diffuse reflectance tissue phantom and the Intralipid stock used in these studies was prepared with no glycerol.

Figure 7:
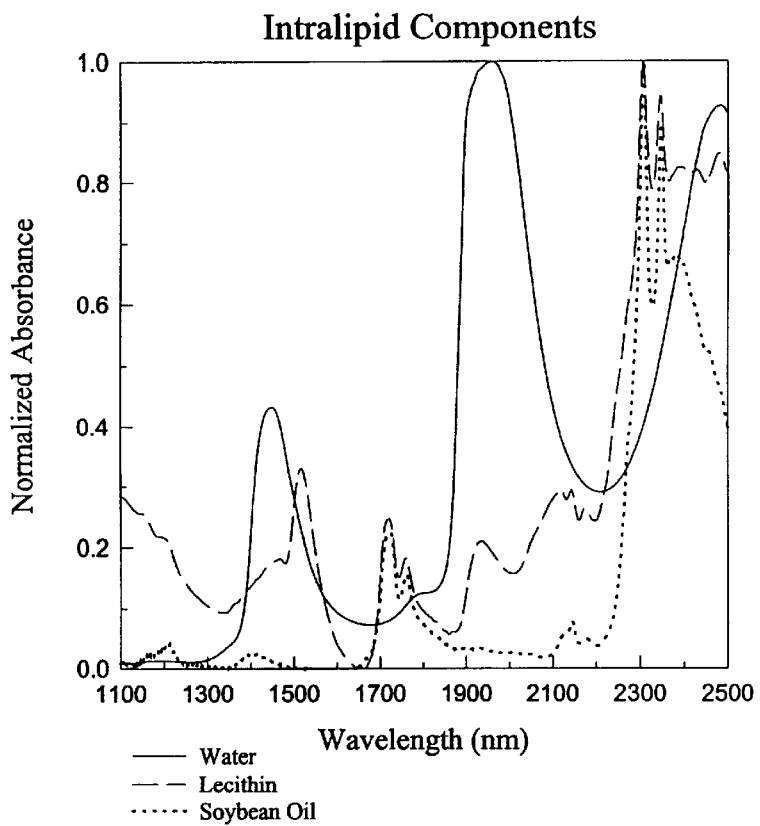
FIG. 7 is a summary of the commercial Intralipid components (water, soybean oil and lecithin) less glycerol in the form of normalized absorbance spectra.

A summary of the commercial Intralipid components, except glycerol, is presented in FIG. 7 in the form of normalized absorbance scans.

Tissue Phantom (Intra-serum) Preparation

Figure 8:
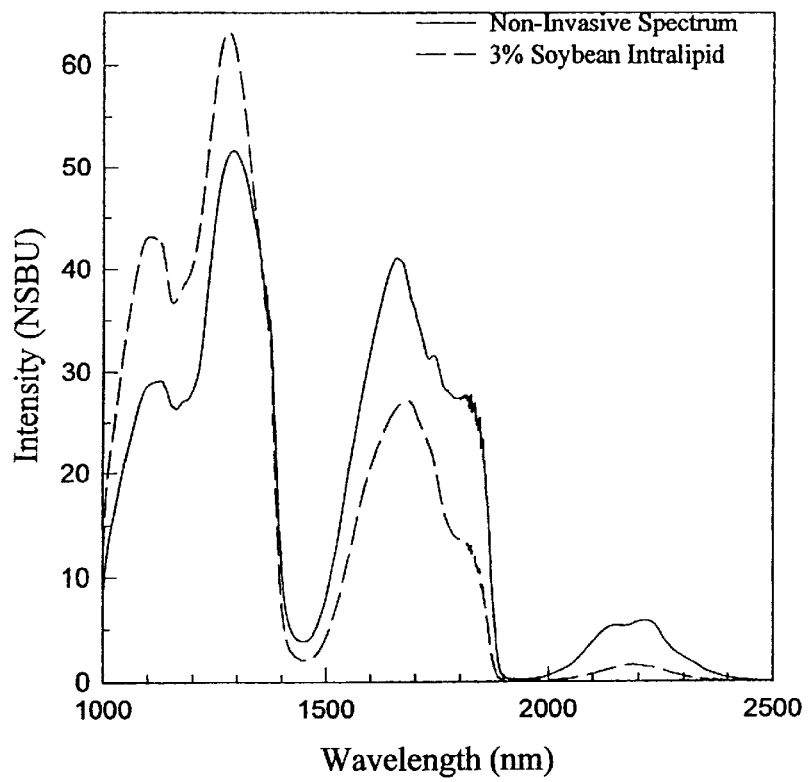
FIG. 8 shows a diffuse reflectance spectrum of a 3% solution of commercial Intralipid along with a diffuse reflectance spectrum of a human forearm.

A diffuse reflectance scan of a 3% solution of commercial Intralipid is presented in FIG. 8 along with a diffuse reflectance scan of a human forearm. Notably, the intensity of the soybean based commercial Intralipid is lower than that of the arm in the 2$^{nd}$ overtone region (1000 to 1450 nm) and combination band region (2000 to 2500 nm) but higher in the 1$^{st}$ overtone region (1450 to 2000 nm). To match the intensity of the arm in the combination band region, an Intralipid solution of 15% is required. This causes far too much light to be collected in the 2$^{nd}$ and 1$^{st}$ overtone region. In addition, in the combination band region, a commercial Intralipid solution of 0.5% is required to match the reduced scattering coefficient of the arm. Clearly, the absorbance and reduced scattering coefficients of a given commercially prepared soybean oil based Intralipid solution can not be made to match the properties of a diffuse reflectance scan of the arm in more than a single region. In addition, glycerol in commercially prepared Intralipid is not a component of skin and its near-IR absorbance bands interfere with glucose.

Figure 9:
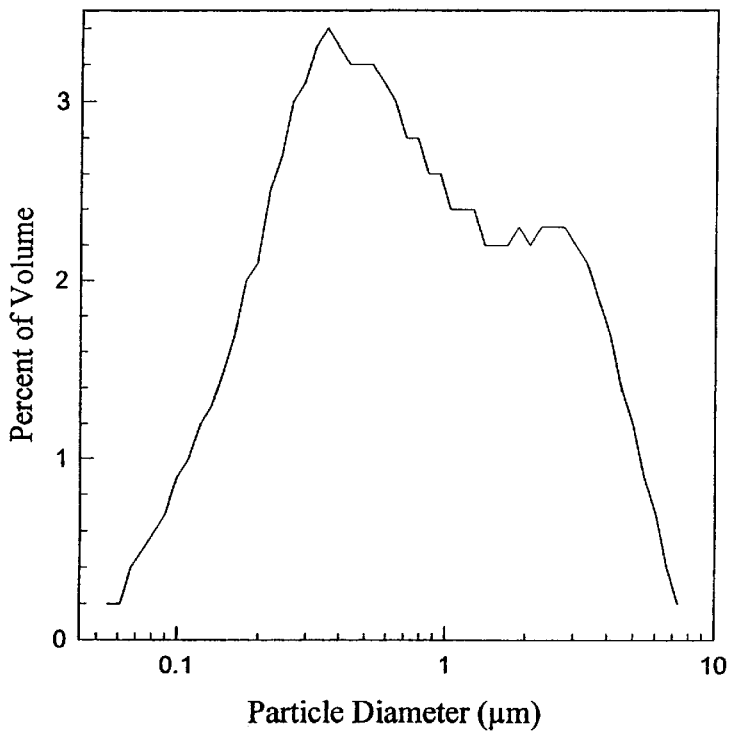
FIG. 9 shows the bimodal particle size distribution of an Intra-serum sample prepared with castor oil with peaks centered at 0.4 and 3.0 μm.

Modified Intralipid and water may be combined to form tissue phantoms with a reduced scattering coefficient to absorbance coefficient ratio ($\mu'_s/\mu_a$) that simulate those of skin. An Intra-serum sample may be prepared with castor oil with a bimodal particle size distribution with peaks centered at 0.4 and 3.0 $\mu$m, see FIG. 9. Studies have shown that the bimodal particle size generates scattering simulating that of the skin tissue of the body. The distance between the peaks of the particle size distribution may be adjusted which affects the scattering. The 0.4 $\mu$m particle size centers simulate the collagen bundles in the skin while the larger particle sizes (1.0 $\mu$m and greater) add scattering that simulates the red blood cells. The change in index of refraction within skin compartments greatly affects scattering. The red blood cells have a water/fat interface with the related index of refraction change and approximately a 1 $\mu$m diameter. The castor oil particles have also have a water/fat interface causing an index of refraction change and approximately a 1 $\mu$m diameter particle size.

Figure 10A:
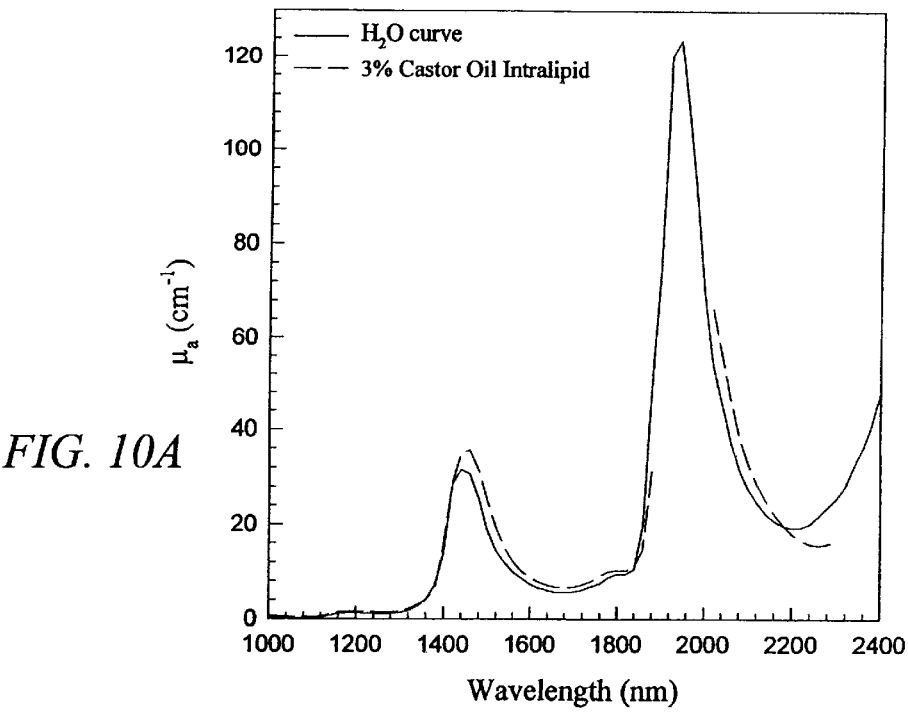
FIG. 10A shows the absorption coefficient of a 3% castor oil based Intralipid and the absorbance of water.
Figure 10B:
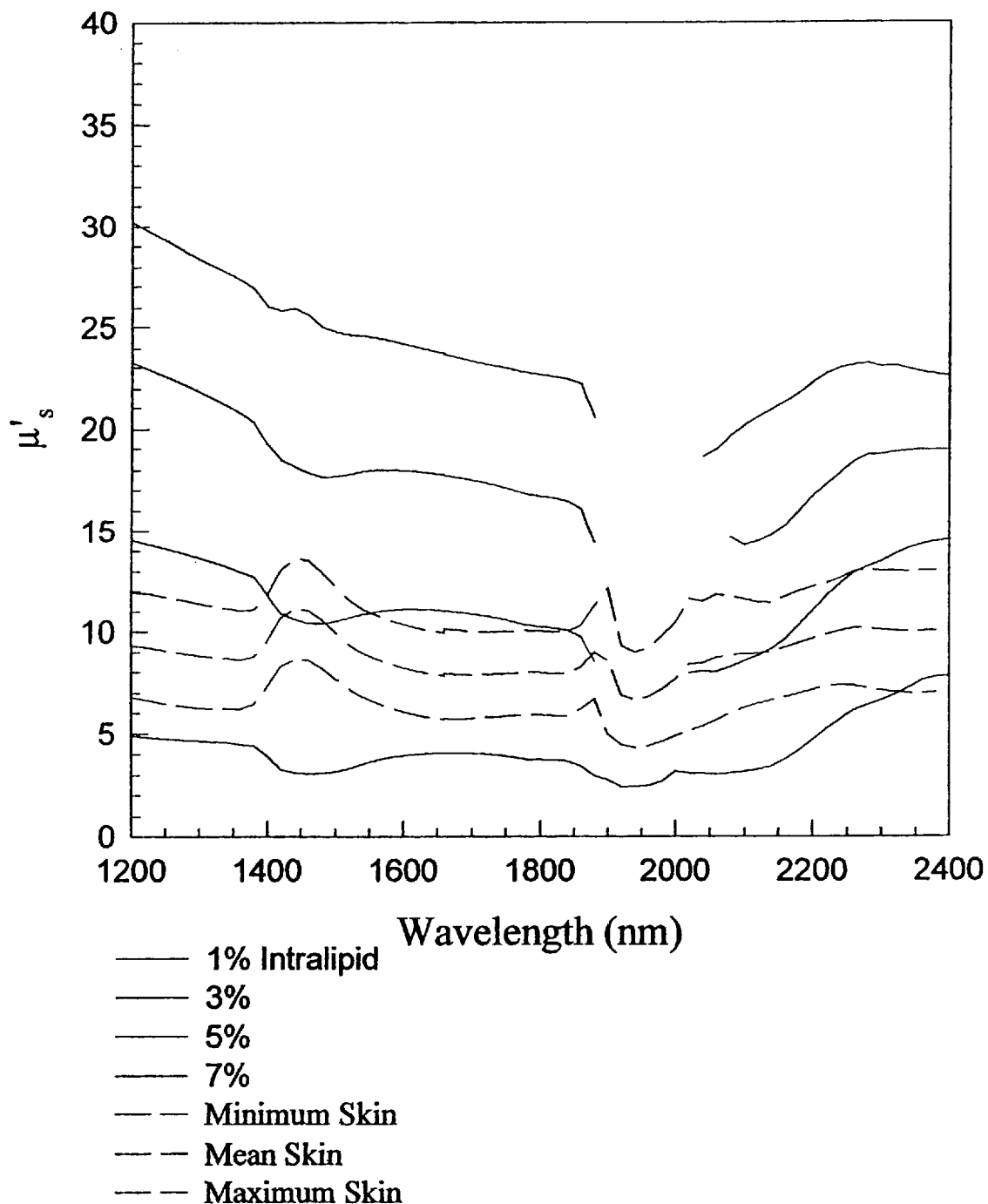
FIG. 10B shows the reduced scattering coefficient of the prepared Intralipid, without glycerol and of human skin.

Intralipid prepared with castor oil has absorbance and reduced scattering coefficients that model those of skin tissue. As expected since Intralipid is primarily composed of water, the absorption coefficient of a 3% Intralipid sample prepared with the bimodal castor oil particle size distribution shows large values where water absorbs, FIG. 10A. The reduced scattering coefficient of this prepared Intralipid was measured at 1, 3, 5 and 7% from 1000 to 2400 nm, FIG. 10B. A range of reduced scattering coefficients for skin are overlaid on this figure. The 2 to 3% Intralipid values fall within the range of values determined for skin. Combined, these figures demonstrate that the absorption and reduced scattering coefficient of 2 to 3% castor oil based Intralipid closely match skin tissue.

Additional Intra-Serum Constituents

Figure 11:
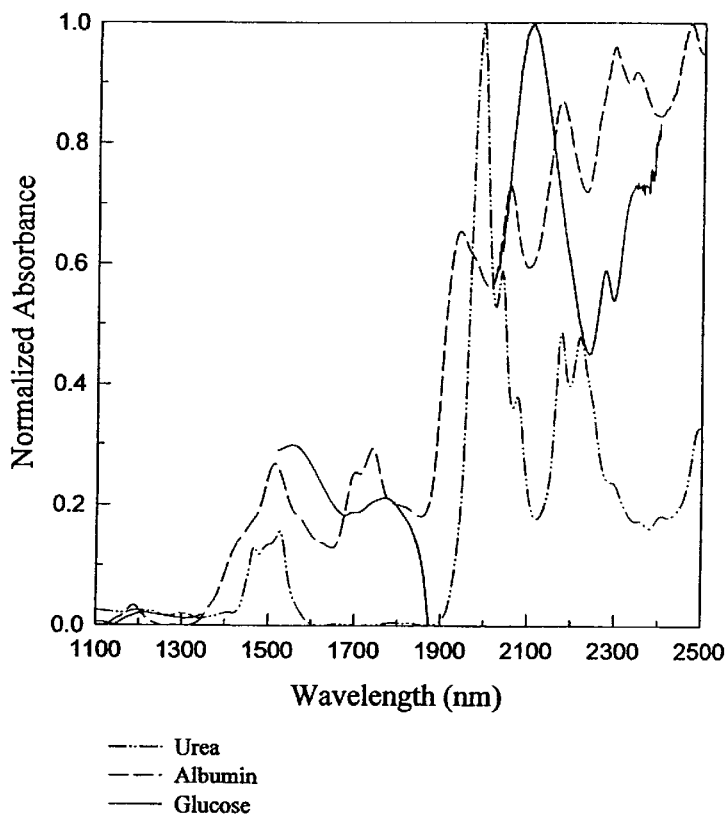
FIG. 11 is a summary of the prepared Intra-serum components in the form of normalized absorbance spectra.

The absorption and scattering coefficients of skin are well modeled with water and Intralipid solutions; however, skin and blood contain several additional near-IR absorbers which behave as interferences in glucose determinations. Collagen and elastin proteins are present in skin with collagen making up approximately 75% of the dry weight of skin and elastin being the next largest component. After water, albumin protein is the primary constituent by mass in blood. Albumin, collagen and elastin have similar absorbances in the near-IR as they are all proteins, data not presented. Since albumin is soluble in water, it is selected to be included in the tissue phantom as an interfering constituent simulating collagen and elastin, FIG. 11. Urea, which has absorbance bands in the combination band and $2^{nd}$ overtone spectral regions, is added to the tissue phantom as an additional interference present in the body, FIG. 11.

A pure component spectrum of glucose is generated using multivariate curve resolution (see R. Tauler, B. Kowalski, S. Fleming, Analytical Chemistry, vol. 65, pp. 2040–2047 (1993)). Glucose and water spectra were collected in transmittance mode with a 1-mm pathlength with glucose concentrations ranging from 0 to 15,000 mg/dL at 1000 mg/dL intervals. Using this data, a calculated pure component glucose spectrum is generated, FIG. 11. The gaps in the resulting spectrum are where the large water band led to unacceptable certainty of the glucose spectrum. The resulting spectrum was verified using multivariate curve resolution on data sets using multiple analytes, with different spectrometers and with varying detectors. Notably, the signal strength for a fixed pathlength is largest in the combination band region, roughly a third the strength in the first overtone region, and small but identifiable in the second overtone region. This spectrum is used in conjunction with calculated net optical pathlengths to generate the expected signal level in the resulting spectra, data not shown.

Experimental Design

The Intra-serum samples are composed of water, Intralipid (soybean oil, lecithin and water), albumin, urea and glucose. If only glucose and Intralipid were present, then as the glucose concentration increased in concentration the Intralipid concentration would be necessarily inversely correlated. The addition of multiple constituents allows the glucose concentration to be uncorrelated with all other sample constituents allowing for critical interpretation of multivariate analyses of the subsequent spectral data sets. The albumin concentration may be kept low and the urea concentration may be kept high, allowing further decorrelation of the concentrations of the components in the experimental design utilized.

The Intra-serum samples have absorption and reduced scattering coefficients approximating that of skin tissue. In addition, the combination of water, modified Intralipid containing long chain fatty acids, albumin, urea and glucose represent all of the major near-IR absorbers of blood and of skin tissue. Finally, the concentration of each constituent may be varied independently from sample to sample. Combined, this allows for a family of samples to be created that allows for the feasibility testing of noninvasive diffuse reflectance near-IR determinations of glucose.

Intra-Serum Tissue Phantom (Summary)

A family of samples have been invented that match the skin layers (stratum corneum, epidermis and dermis) of the human body in terms of absorbance, the absorption coefficient ($\mu_a$), the reduced scattering coefficient ($\mu'_s$), and in terms of layers of samples matching each of the varying skin layers in chemical composition. These samples use lipid emulsions that are suspended into aqueous solutions using emulsifiers such as lecithin, i.e. a phosphatidylcholine. One family of these samples is commercially sold under the class name of Intralipid. In this disclosure, the names Intra-serum and Intra-gel are used to refer to the class of newly invented samples.

A modified version of a commercial product known as Intralipid is used in the manufacturing of the Intra-serum and Intra-gel. However, the Intralipid used in the production of Intra-gel and Intra-serum has multiple fundamental differences from the product sold commercially as Intralipid. In particular, the commercial Intralipid contains glycerol (as a nutrient and to prevent freezing), whereas the herein disclosed compound does not contain glycerol because it interferes spectrally with glucose. In addition, the particle size distribution of commercial Intralipid is Gaussian with mean particle sizes of about 0.4 $\mu$m. The particle size distribution of the Intralipid used to create Intra-serum and Intra-gel may be Gaussian with mean particle sizes ranging from 0.2 to 2.0 $\mu$m. However, in the preferred embodiment of the invention the particle size distribution is bimodal in nature. In one case, the mean particle sizes are 0.4 and 3.0 $\mu$m. To make larger particle sizes, the base oil must be altered from soybean to castor oil. Large emulsion particle sizes cannot be made in a stable fashion with soybean oil but can be made with castor oil. Another difference is that Intralipid is sold commercially in 10, 20 and 30% concentrations. While the Intralipid stock herein disclosed may be prepared in these concentrations, the final percentages in the Intra-serum and Intra-gel that most closely match the body range from 2–4%.

Intra-serum uses a modified stock Intralipid in preparation. Additional components are added to the solution to simulate human serum and skin tissue further. In particular, the suspended oil solution is spiked with basis set components: albumin, globulin, urea and glucose and other organic compounds such as collagen, elastin, globulin, lactic acid and bilirubin. In addition, electrolytes may be added such as $Na^+$, $K^+$ and $Cl^-$. The resulting family of Intra-serum samples may be prepared with any concentration of any of the components. Samples within the class may be prepared with no correlation between samples (demonstrated below). In addition, samples may be run in a random order. In the noninvasive glucose problem, this allows samples in which the scattering and absorbance coefficients match that of skin, in which all major interferences present in the skin are present in the sample (basis set components), in which no correlation exists between analytes or interferences (a cause of major concern in multivariate analysis using techniques such as partial least squares (PLS) or principal component regression (PCR)), and in which the samples may be run in a random order eliminating concerns of correlation of analyte components with time (again a major concern when multivariate analysis is used). A major benefit of the Intra-serum samples is that all major components of skin tissue in terms of absorbance are present while additional components not present in skin (such as polystyrene which absorbs strongly in the near-IR) are not present.

Intra-gel samples are prepared with Intra-serum samples and as such retain all of the benefits of the Intra-serum samples. In addition, Intra-gel samples have several other benefits. Intra-gel samples are created by crosslinking Intra-serum samples with a suitable crosslinking agent such as gelatin. This results in a solid sample that may be used as a standard in diffuse reflectance, transflectance or transmission mode. The water concentration of the Intra-gel may be brought down to that matching the body due to the crosslinking. The collagen and elastin used as the crosslinking agent are naturally present in a crosslinked form in skin. The Intra-gel samples have the additional advantage of being stable.

The Intra-gel samples are solids that are readily cut or sliced. Therefore, Intra-gel layers of varying thickness may be prepared and stacked to simulate varying layers of the skin. In particular, each layer of skin has its own unique chemical makeup. The concentrations of the analytes of interest and interfering compounds may be matched in the stacked Intra-gel samples. In addition, each layer of skin has its own thickness, which again may be matched or varied with Intra-gel samples. Each layer of skin also has its own index of refraction and particle size distribution that may be matched with the Intra-gel samples. The resulting samples are flexible in each analyte's concentration and match the skin layers of the body in terms of reduced scattering and absorbance coefficients, $\mu'_s$ and $\mu_a$ resulting in excellent tissue phantoms. In view of the disclosure herein, one skilled in the art can readily modify these Intra-gel samples to match additional tissues and internal organs in any of the human body, animal body or other tissues, e.g. vegetable tissues.

In summary, a family of samples has been created that are composed of the major near-IR absorbing components of human skin. Each near-IR absorbing component of these samples may be varied in concentration in a quantitative fashion independently of other components in the sample. In this way, any correlation between components can be removed. Because all major near-IR absorbing components of skin are present, and they can all be varied in concentration, the effect of each component on spectroscopic analysis of skin may be determined. Such procedures cannot be performed on real skin due to lack of quantitative knowledge of each component.

THE PREFERRED EMBODIMENT OF THE INVENTION

Introduction

Figure 12:
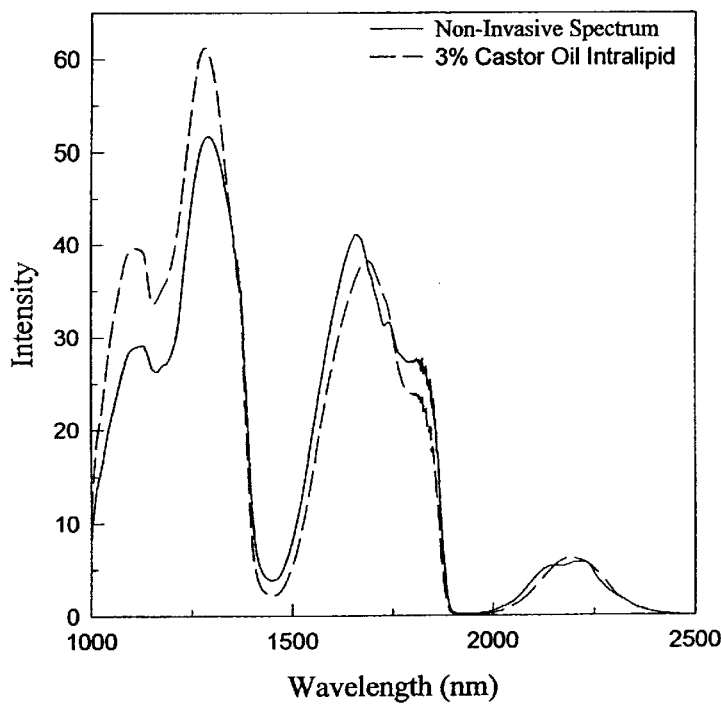
FIG. 12 shows a diffuse reflectance spectrum of a 3% solution of a castor oil based Intralipid solution along with a diffuse reflectance scan of a human forearm.

The preferred embodiment of the invention is the family of samples known collectively as Intra-serum. A near-IR diffuse reflectance spectrum of a human forearm is presented in FIG. 12 along with a diffuse reflectance spectrum of an Intra-serum sample. This Intra-serum sample was prepared with castor oil and has a bimodal particle size distribution with peaks centered at 0.4 and 3.0 $\mu$m. The castor oil droplets are suspended in the aqueous solution with lecithin. The observed intensity in the $2^{nd}$ overtone (1000 to 1450 nm), $1^{st}$ overtone (1450 to 2000) and combination band (2000 to 2500) spectral regions of the human arm is closely modeled by the Intra-serum sample. In particular, water absorbance bands are observed in both at 1450, 1950 and 2600 nm. Fat absorbance bands are observed in both at 1167, 1210, 1391, 1413, 1724, 1760, 2123, 2144, 2347 and 2380 nm. As discussed below, the absorbance bands observed at 1188, 1512, 1734, 1740, 1940, 2174, 2288, 2294, 2342 and 2466 nm are due to protein and may be added as components to the Intra-serum sample. The absorption, $\mu_a$, and reduced scattering, $\mu'_s$, coefficients of a 3% Intra-serum sample match the absorption and scattering coefficients of human forearm skin tissue, see FIGS. 10A and 10B. This solution acts as a base matrix to which additional organic components, such as collagen, elastin, globulin, lactic acid and bilirubin, and electrolytes such as $Na^+$, $K^+$ and $Cl^-$ may be added. Studies may then be run in which interferences and/or analytes are added, removed, or altered in concentration. This allows individual effects to be delineated and quantified.

A family of samples has been generated that simulate near-IR diffuse reflectance spectra of the human body in terms of basic absorption and scattering properties. This allows a number of studies to be run.

First, the basis set is expanded to individual and mixtures of components in a scattering environment. The effect of scattering on the position, magnitude, and shape of each analyte is addressed.

Second, the effect of varying concentrations of scattering elements on a glucose in scattering media study is determined. The effectiveness of existing chemometric tools to deal with scattering satisfactorily is addressed.

Third, this study is repeated with multiple analytes in the scattering medium.

Fourth, the net analyte signal may be calculated, the depth of penetration of the photons can be directly measured and the percent fraction of the photons reaching each depth may be measured. In addition, the total optical pathlength at each frequency may be calculated.

Fifth, with fiber optic probes the radial diffusion of the photons can be measured and the depth of penetration of the photons can be measured in a different manner.

Sixth, a standard sample can be prepared for alignment of the spectrometers using diffusely reflected light. With the correct addition of analytes, this sample could be used as a wavelength standard. This standard sample may be used in calibration transfer procedures.

Seventh, studies can be readily designed in which analyte concentrations correlate to different degrees. The effect of varying degrees of correlation of analytes on PLS models may be addressed.

Eighth, the effect of multiple layers can be addressed. The pathlength and chemical makeup of each layer can be prepared in a known fashion aiding in the development of chemometric tools.

Ninth, glucose may be determined with clinically relevant accuracy and precision in near-IR data sets in diffuse reflectance mode in which the absorption coefficient and scattering coefficient match the body and in which all major near-IR interferences to a noninvasive glucose determination are present at physiological concentrations.

Some studies with simple Intra-Serum samples that simulates the near-IR diffuse reflectance of the body are summarized below. Each study progressively adds complexity to the sample matrix and utilizes instrumentation more appropriate to that used in a noninvasive glucose determination.

Study 1: Preliminary Studies/Purchased Intralipid

In the first study, Intralipid-10% purchased from Baxter is analyzed to demonstrate the effects of Intralipid concentration. Water and fat absorbance bands in Intralipid are identified. In addition, a method of analysis to determine depth of penetration of the photons is demonstrated. It is recognized that the glycerol in the purchased Intralipid prevents glucose in Intralipid studies from being performed and that the particle size limits conclusions that can be drawn from results on studies such as depth of penetration of the photons. These studies may be repeated without glycerol and with the correct particle sizes.

Figure 13:
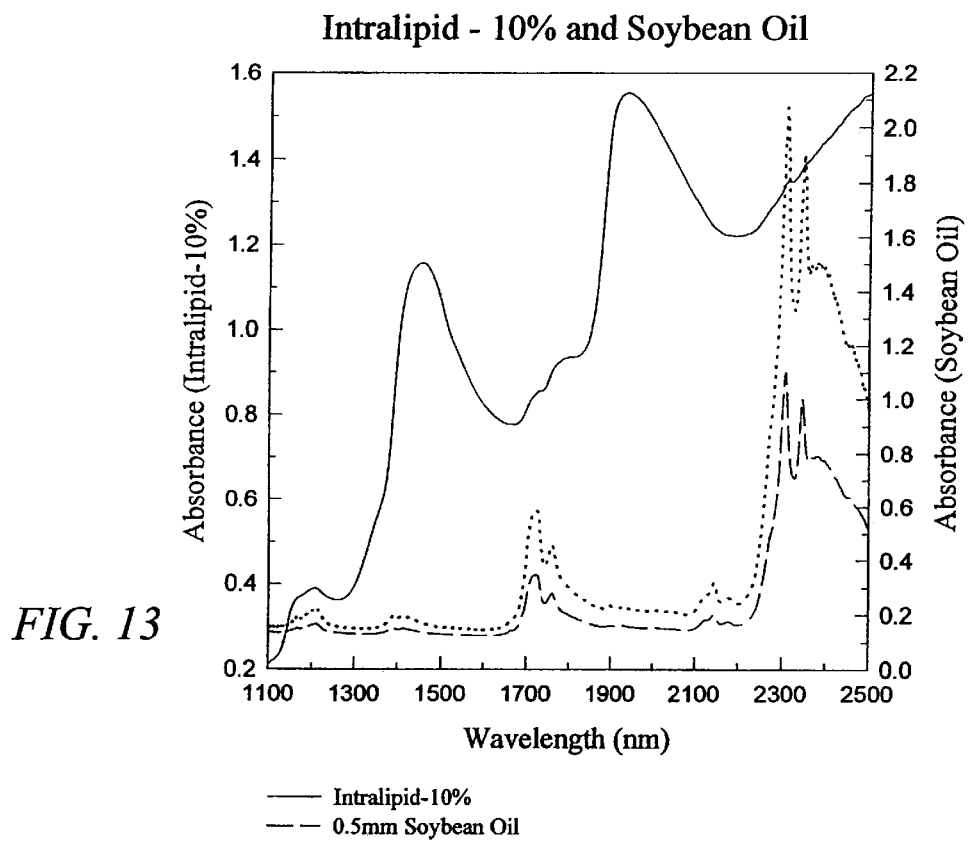
FIG. 13 shows a raw absorbance spectrum of an lntralipid-10% solution and fat absorbance bands from soybean oil.

Raw absorbance spectra of the Intralipid-10% are presented in FIG. 13. The spectra are of varying amounts of the Intralipid-10% standard placed into an aquarium sample cell. The spectra appear as roughly noninvasive spectra. The baseline rises from 0.2 to 1.2 absorbance units from 1100 to 2200 nm as do diffuse reflectance spectra skin. The large water absorbance bands are apparent at 1450, 1890 and 2500 nm. Additional absorbance bands are observed at 1167, 1210, 1724, 1760, 2307 and 2347 nm. These bands exactly correlate with those of pure soybean oil collected in transmittance with a 1.0 mm pathlength on the Magna 860 spectrometer. As shown above, the soybean oil is the scattering center of Intralipid. Therefore, in Intralipid the light is penetrating the scatterer.

Figure 14:
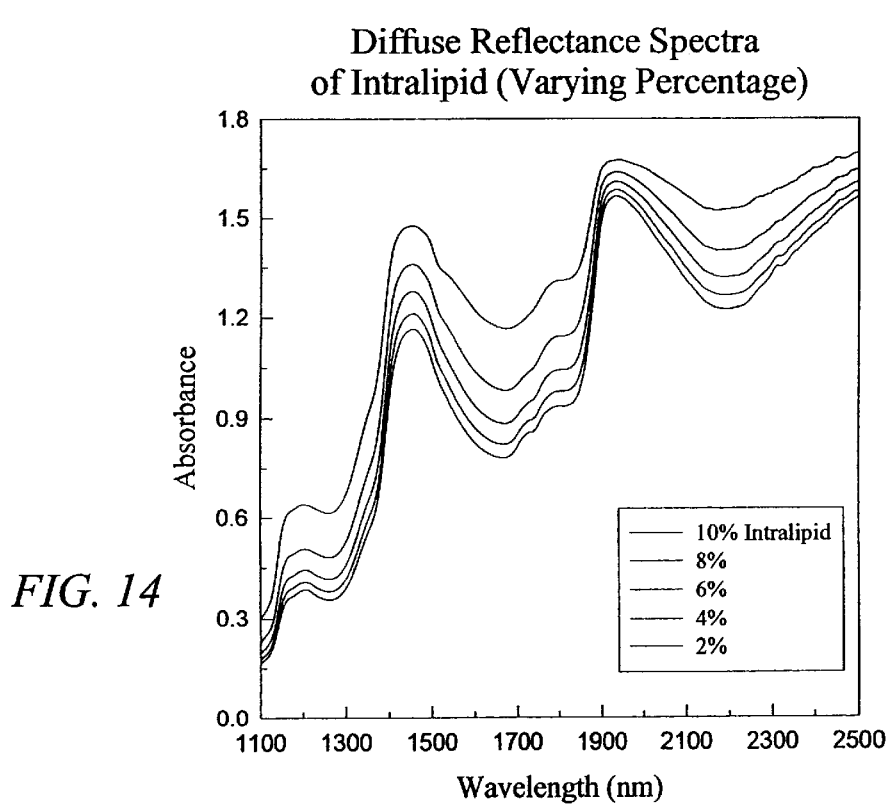
FIG. 14 shows diffuse reflectance spectra of Intralipid ranging from 2 to 10%.
Figure 15:
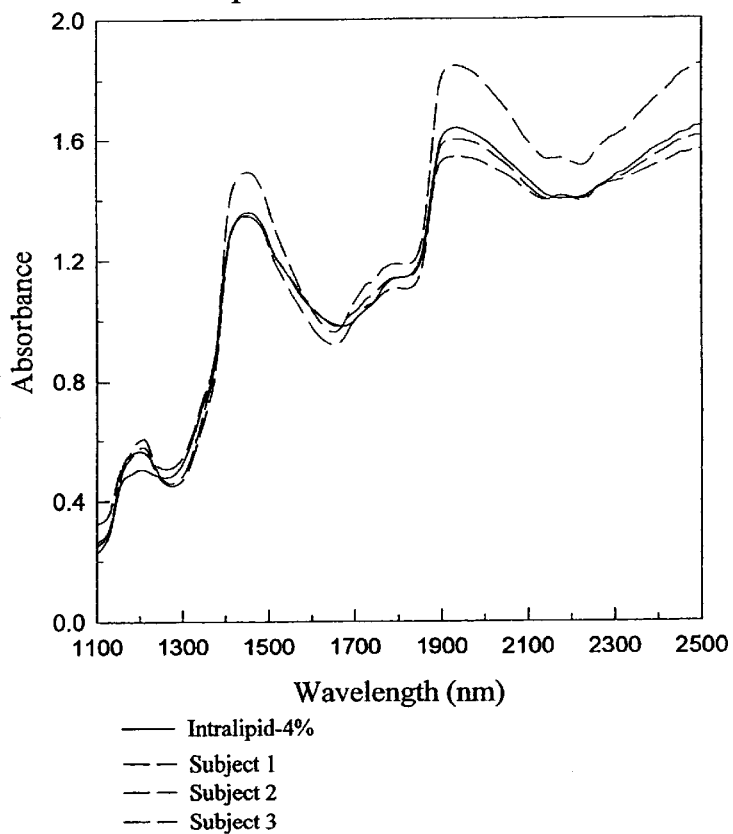
FIG. 15 shows diffuse reflectance noninvasive spectra of three individuals overlaid with an Intralipid-4% spectrum.

The spectral profile of an Intralipid-10% solution shows less absorbance and hence more scattering of light than the body. Diffuse reflectance spectra of Intralipid ranging from 2 to 10% are collected and presented in FIG. 14. As the amount of oil is decreased, the number of scatterers decreases and the average pathlength increases. Therefore, the absorbance increases as the Intralipid percentage is decreased. In FIG. 15 noninvasive scans from three individuals collected on the NIRS in diffuse reflectance are overlaid with the Intralipid-4% spectrum. With the exception of the fat absorbance band at 1210 nm, the Intralipid-4% skin simulant is within the variance of these three noninvasive scans. The absorbance band at 1210 nm is due to fat layers in the body. This factor is simulated when multiple cross-linked layers are used to simulate the skin.

Figure 16:
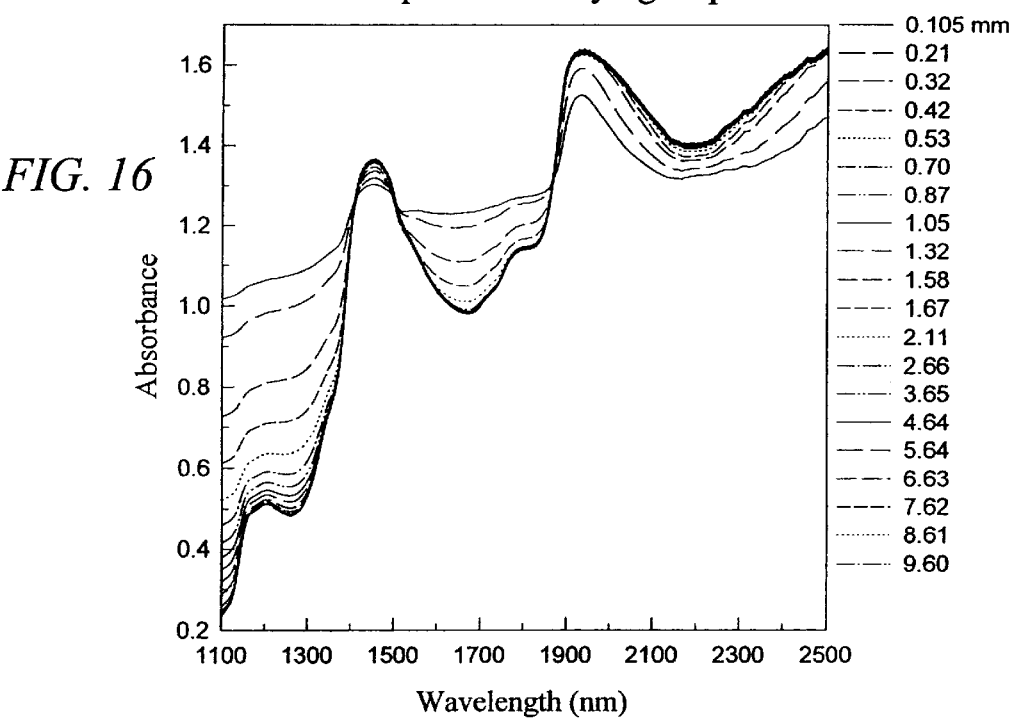
FIG. 16 shows diffuse reflectance spectra of lntralipid-4% with varying depths of solution ranging from 0.10 to 9.60 mm.

This first example of Intralipid simulating the body allows preliminary studies to be run that measure the migration of the photons in the body. The first such experiment showing the depth of penetration of the photons is presented here. The penetration depth of the photons into the Intralipid-4% solution is examined as a function of frequency. Diffuse reflectance spectra of the Intralipid-4% with an infinite depth have spectra that closely model noninvasive scans of the body. Therefore, if the penetration depth of the photons into the Intralipid-4% can be measured, an estimate of the depth of penetration of the photons in the body can be obtained. Spectra of Intralipid with varying depths of solution ranging from 0.10 to 9.60 mm are presented in FIG. 16. Photons penetrated through a sapphire window into the bottom of the aquarium sample cell. Some photons through diffuse reflectance are detected, others reach the air sample interface at the top of the sample where they are either reflected or lost. At 1100 and 1700 nm, the absorbance is observed to decrease as the depth of the Intralipid solution is increased. When the depth of the solution is small relative to absorbing and scattering, photons are lost to the air at the top of the sample. This results in an artificially high absorbance. As the depth of the Intralipid solution increases, fewer photons reach the air/Intralipid interface and more photons are scattered back to the detector, resulting in a lower measured absorbance. As the depth increases to infinity, the absorbance approaches a constant value. At 2200 nm, the absorbance is observed to increase as the depth of the Intralipid solution is increased. This is due to the backscattered light originating at the Intralipid/air interface (due to refractive index differences).

Figure 17:
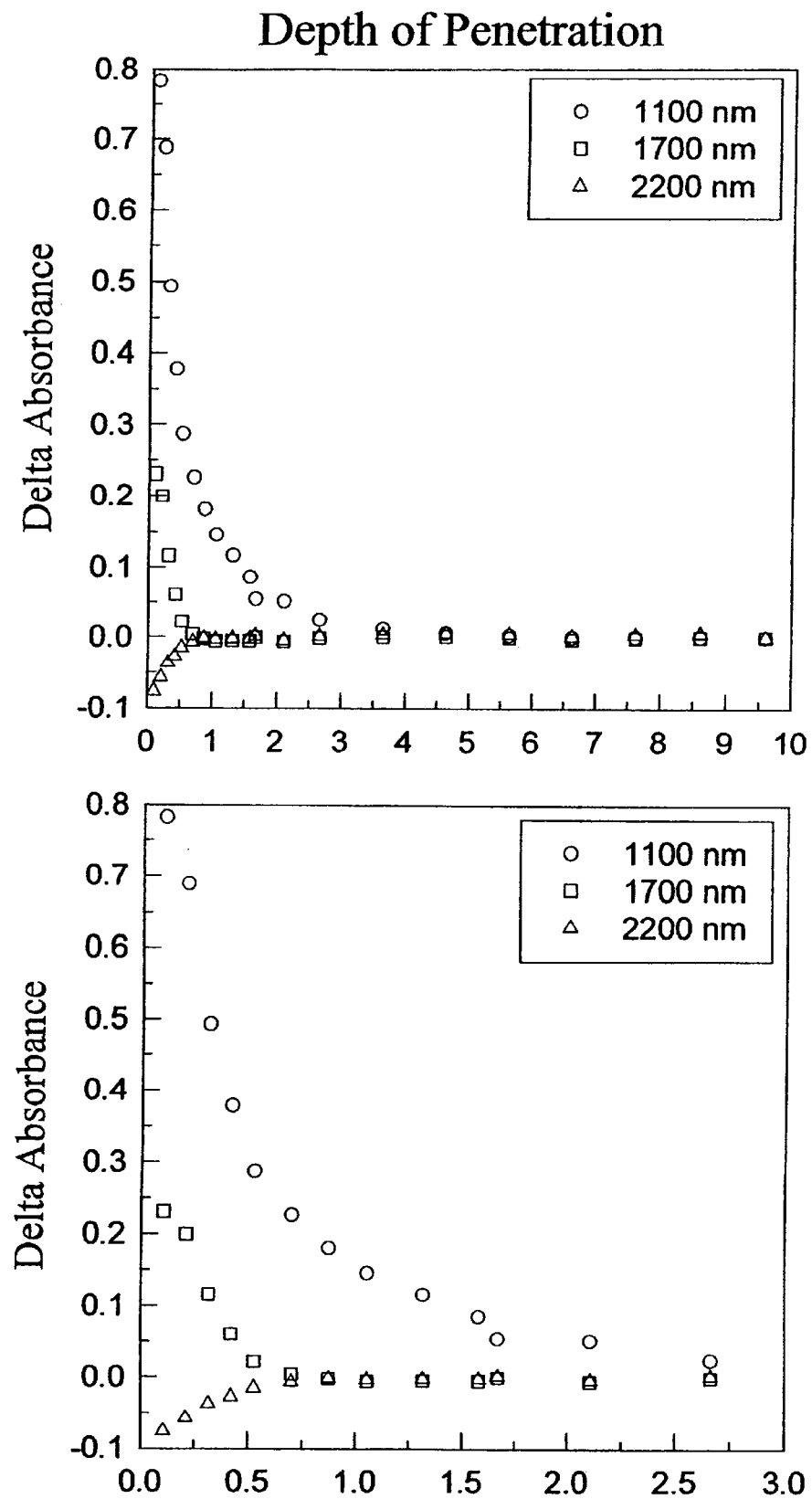
FIG. 17 shows using absorbance as a function of depth that the depth of penetration of the photons can be measured as a function of frequency by using the difference in absorbance. This is demonstrated at 1100, 1700 and 2200 nm representing the second overtone, first overtone and combination band regions.

Using the absorbance as a function of depth, the depth of penetration of the photons can be measured as a function of frequency. The absorbance at each depth is subtracted from the absorbance at infinite depth (9.60 mm). The difference in absorbance from the infinite depth is a measure of the number of photons reaching the tested depth. FIG. 17 shows this difference in absorbance at 1100, 1700 and 2200 nm representing the second overtone, first overtone and combination band regions. In the second overtone region, photons are observed to penetrate to approximately 5 mm and still return to the incident surface. Note that the proportion of the photons reaching each depth from 0.1 to 5 mm can be calculated from this data by using the percent of integrated area to that depth versus the integrated area to infinite depth. In the first overtone and combination band regions, photons penetrate to 0.7 mm. Note that the pathlength due to scattering and total pathlength at each of these maximum penetration depths can be calculated. For example, at 2200 nm the absorbance at infinite depth is 1.40. The oil absorbance is minimal at 2200 nm versus water. Because water has an absorbance of 0.82 at 2200 nm for a 1 mm pathlength, the pathlength of the photons is 1.7 mm (1.40/0.82) at 2200 nm for the infinite depth sample. Because the photons are penetrating 0.7 mm the pathlength off of the straight transmittance path is 0.3 (1.7–0.7*2). Similarly, at 1700 nm the absorbance of the Intralipid is 1.01 and water has an absorbance of 0.23 per millimeter of pathlength. Therefore, the total pathlength is 4.5 mm even though the depth of penetration is only 0.7 mm. The pathlength off of the straight transmittance path is correspondingly large at 3.1 mm (4.5–0.7*2). This is a measure of how far the samples diffuse radially. Note that the radial diffusion of the photons can be measured directly using Intralipid solutions and a collection fiber optic accessory that is translated away for the incident light.

This methodology allows the depth of penetration of the photons in the body to be measured. Replacing the Intralipid sample with a series of Intra-gel slabs that match the skin layers will allow a more accurate measurement of depth of penetration of photons in the body.

Following are data sets created and analyzed using Intraserum. With each study, the complexity of the matrix is expanded and the instrumentation used is improved.

Study 2: Glucose. Water and Modified Intralipid in Transmittance

Introduction

Study 2 builds upon knowledge gained in Study 1. A data set is generated in which glucose may be determined in the presence of a scattering medium.

When performing multivariate analysis on spectra, there exists a sample preparation problem in which the analyte concentration correlates or inversely correlates with another component concentration. In the resulting analysis, it must be demonstrated that the analyte is being determined rather than the corresponding analyte concentration. For example, imagine ten samples of a single milk stock solution being spiked with glucose ranging from 100 to 1000 mg/dL at 100 mg/dL intervals. The resulting scattering concentration of the milk, proteins in the milk, water in milk, on so on correlate inversely with the glucose concentration in the milk. In other words, as additional glucose is added per unit volume, the other components are proportionally diluted. A partial least squares analysis can then find differences in the spectra that correlate with any of these other components and incorrectly identify them as attributable to glucose. This is a well-known and serious complication.

Several methods exist to eliminate the concentration correlation issue. In this study, water is added to the sample, after the glucose in water has been added, in a manner that the resulting concentration of scattering centers has no correlation with the glucose concentration. In any three component system such as this, two components must correlate. In this case, the glucose concentration correlates inversely with the water concentration. This experimental design places the burden on the scientist to prove that glucose is being determined rather than the water concentration. As will be shown, this is readily accomplished by examining the standard error of prediction (SEP) versus spectral loadings. This is done in combination with selecting spectral ranges that contain or do not contain glucose absorbance bands and interpreting the resulting SEP's.

Another method of breaking the concentration correlation issue is by adding additional analytes in a designed experiment until correlation coefficients are reduced to an acceptable level. This is demonstrated in subsequent studies.

This procedure is performed to determine if glucose can be measured using near-IR spectra when the concentration of the scattering components does not correlate with the glucose concentration. This experiment is initially run in transmittance mode and is then repeated in diffuse reflectance mode.

Experimental

Sample Preparation

Three stock solutions were prepared. A 5142 mg/dL glucose in dl water stock solution was prepared. A 3.6 g/dL preparatory stock solution of laboratory grade lecithin in dl water was prepared. The soybean oil was obtained from a local health store. A 5.66% (vol/vol) Intralipid stock solution was prepared without glycerol by pipetting 50 mL of soybean oil and 833.33 mL of the lecithin stock solution directly into a blender. The blender was run on low speed in blend mode for ten minutes. The ten-minute blending cycle was repeated three times with a ten-minute pause between each cycle to prevent heating of the sample.

A total of 64 glucose in Intralipid samples were then prepared over a two day period. A 7×7 star design of sample concentrations was prepared. Glucose concentrations ranged from 0 to 599.04 mg/dL at 85.60 mg/dL intervals. The Intralipid concentration ranged from 0 to 0.8835 (vol/vol) at 0.126 (vol/vol) increments. All samples were brought to a total volume of 20 mL with dl water. All samples were prepared immediately prior to analysis.

Data Collection

Spectra were collected on a NIRS 5000 in transmission mode. The transmission module was equipped with a single PbS detector. The sample cell is a standard 1 mm pathlength open top quartz cuvette from Foss. Data were collected over the 1100 to 2500 nm spectral region. A total of 64 co-added spectra were used for each of four replicate spectra. A dl water sample was collected with every two samples. Data collection continued for a period of 22 hours in a single day.

Results and Discussion

Figure 18:
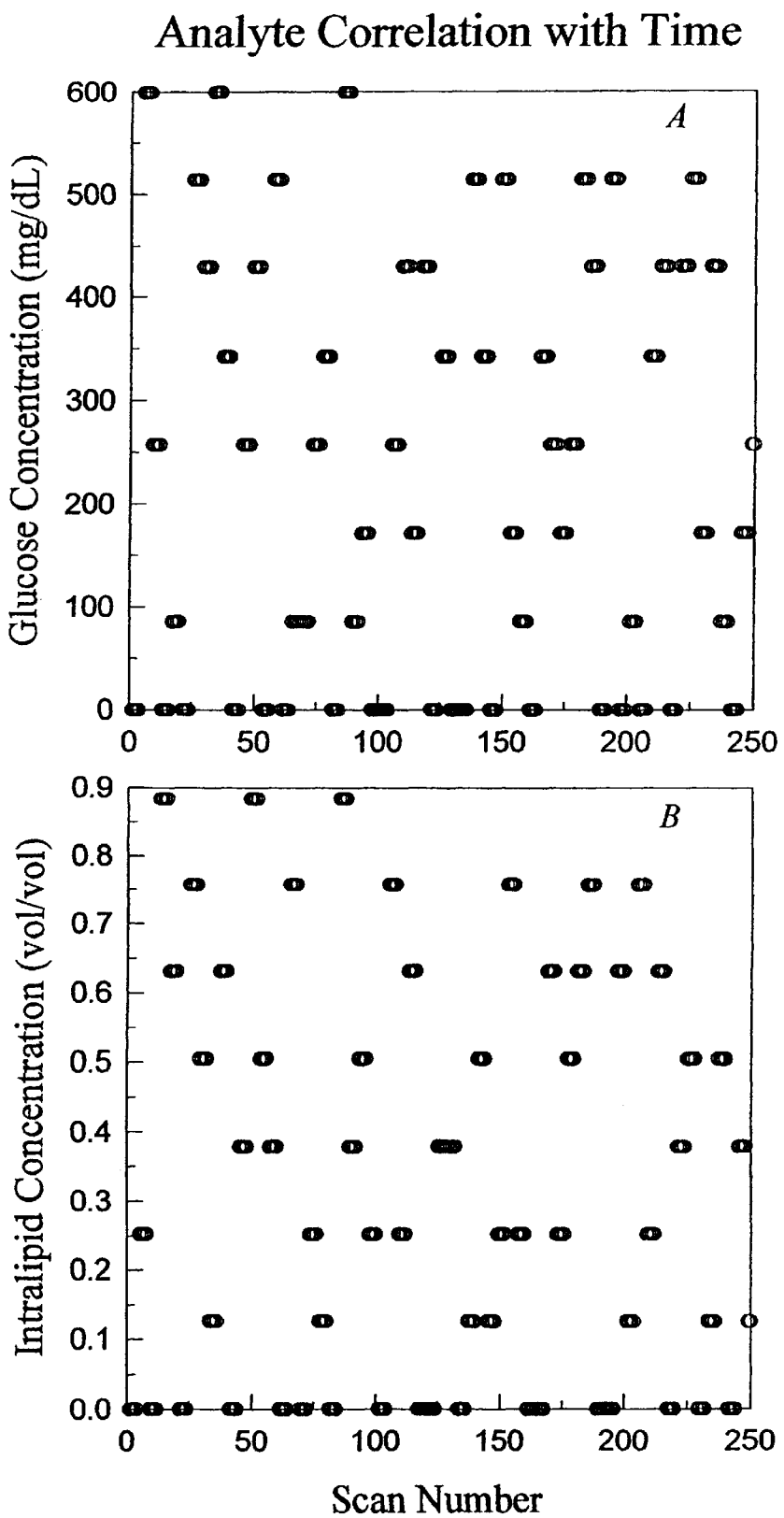
FIGS. 18A and 18B show glucose and Intralipid concentrations for each sample plotted as a function of time (scan number)

In Study 2, the 64 samples of Intralipid-6% prepared without glycerol were spiked with glucose in water and with dI water. The resulting samples have no correlation between the glucose concentration and the oil or scattering concentration. The samples were run in a random order with respect to both the glucose and Intralipid concentrations. The glucose and Intralipid concentrations for each sample are plotted as a function of time in FIGS. 18A and B, respectively. These graphs demonstrate that the glucose concentrations and Intralipid concentrations are random versus time. This eliminates the concern of the glucose concentration as a function of time tracking an outside influence on the spectra such as laboratory temperature or source voltage. In order for PLS to correlate the effect on the spectra of the unknown parameter with glucose, the unknown parameter would have to vary with a high correlation to the random glucose concentrations with time.

Figure 19:
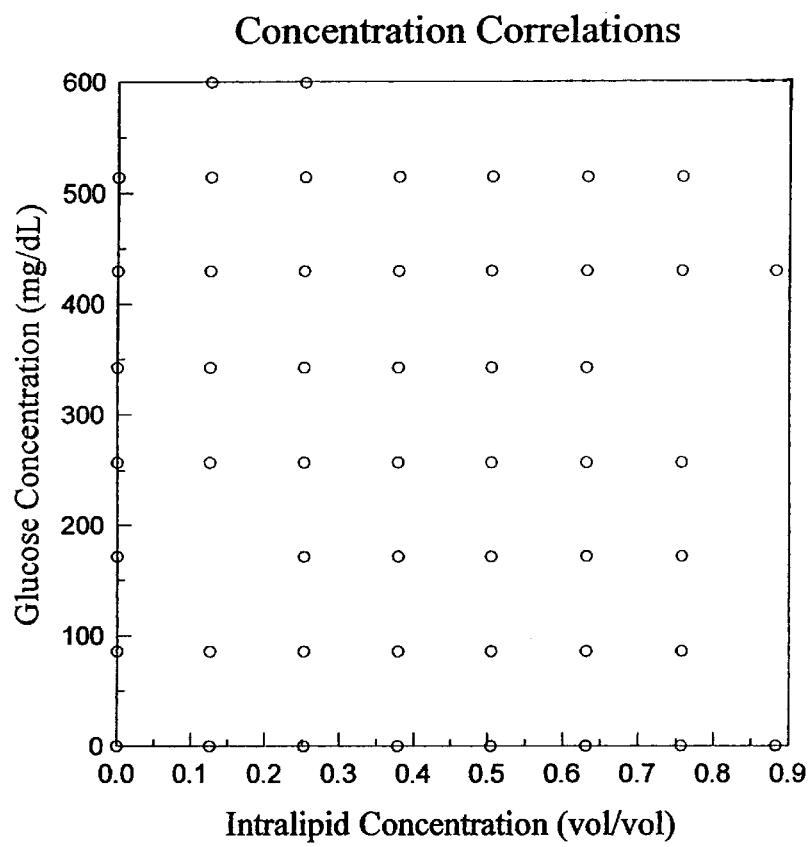
FIG. 19 shows the glucose concentration plotted versus the Intralipid concentration for each sample.

For each sample, the glucose concentration is plotted versus the Intralipid concentration, as shown in FIG. 19. The experimental design is a 7×7 star design. One sample was discarded because all predictions of glucose were 0 mg/dL. It is believed that glucose was not spiked into this sample. In addition, the data for a single sample was lost in data transfer. Five additional samples were run with glucose concentrations of 600 mg/dL or with Intralipid concentrations of 0.88 (vol/vol). This figure demonstrates that the glucose concentration does not correlate with the Intralipid concentration. Therefore, there is no risk of PLS modeling changes in the fat/oil concentration and correlating them with the glucose concentrations. This is critical because the fat/oil absorbance bands have spectral characteristics (mean spectral location and standard deviation of peak width) similar to those of glucose and are not readily separated by chemometric analysis. Using this experimental design, the glucose concentration correlates inversely with the water concentration. Therefore, the analyst is required to demonstrate that glucose is being determined in the analysis rather than the displacement of water.

Figure 20:
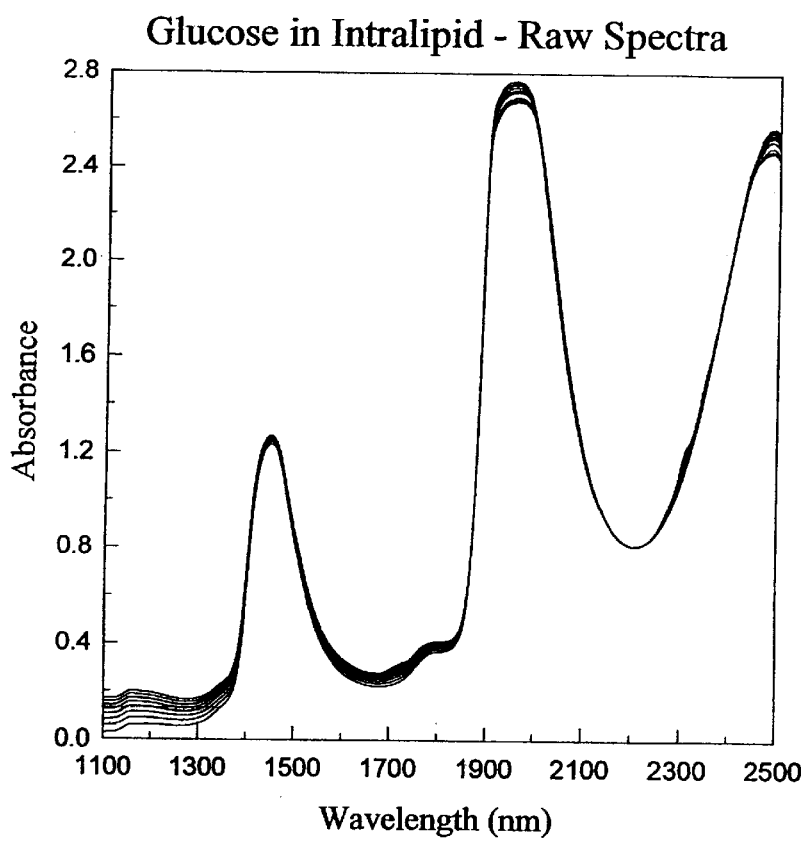
FIG. 20 shows the raw absorbance spectra of the glucose in Intralipid samples.
Figure 21:
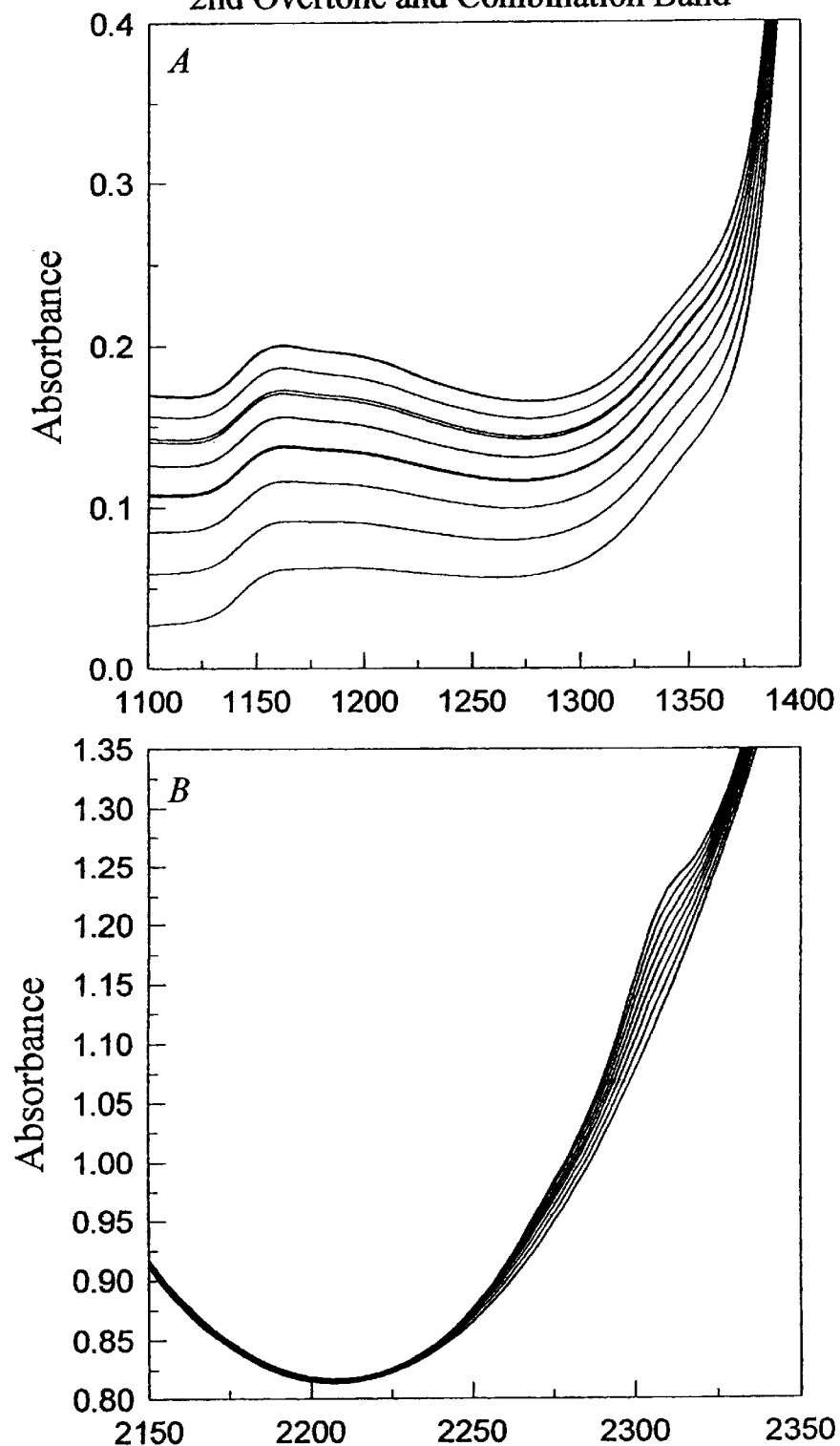
FIG. 21A shows the second overtone region expanded, where the eight different Intralipid concentrations are readily visible in the 1100 to 1300 nm region which is dominated by scattering.
FIG. 21B shows the fat/oil absorbance band expanded, where the eight different concentrations of Intralipid are readily apparent at 2308 nm.
Figure 22:
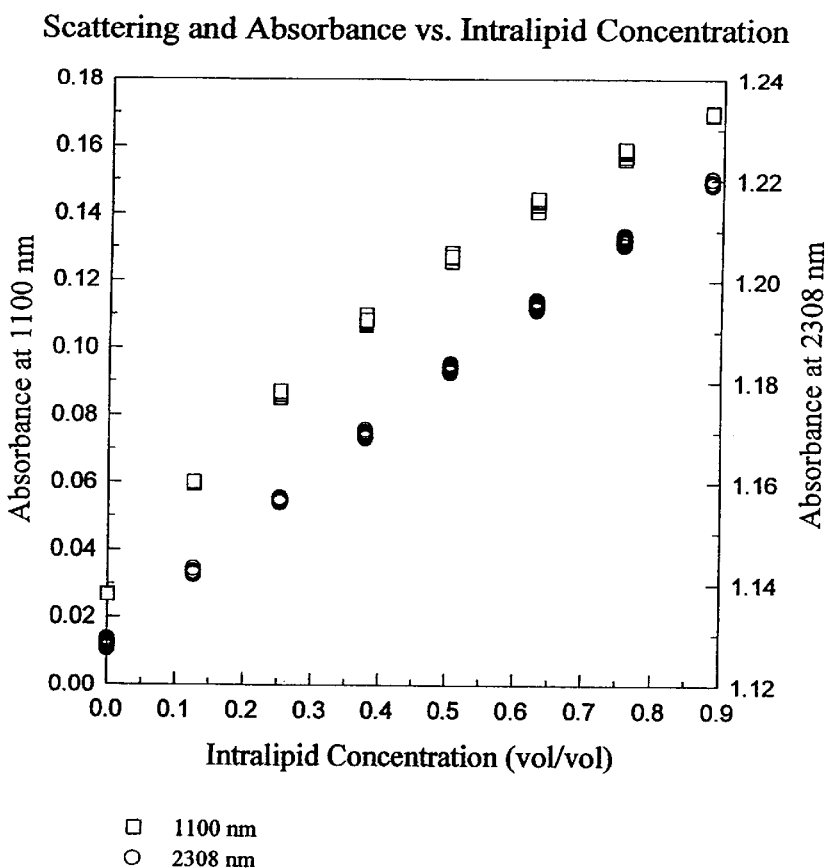
FIG. 22 shows the absorbance at 1100 and 2308 nm plotted against the Intralipid concentration for each sample.

The raw absorbance spectra of the glucose in Intralipid samples are presented in FIG. 20. The absorbances approximate 0.8 and 0.3 in the combination and $1^{st}$ overtone region, respectively. In the absence of scattering, the pathlength, calculated signal levels and noise levels and prior studies suggest that glucose should be predicted with less than 1 mM (18 mg/dL) of error. The second overtone region is expanded in FIG. 21A. The eight different Intralipid concentrations are readily visible in the 1100 to 1300 nm region, which is dominated by scattering. The fat/oil absorbance band is expanded in FIG. 21B. Again the eight different concentrations of Intralipid are readily apparent at 2308 nm. The absorbance at 1100 and 2308 nm is plotted against the Intralipid concentration for each sample in FIG. 22. At 2308 nm, the absorbance is observed to increase nearly linearly as expected by Beer's law and serves to demonstrate that absorbance is dominating over scattering in this spectral region. The absorbance at 1100 nm also increases with increasing Intralipid concentration. The asymptotic nature of the change in absorbance may be an indication of light scattering being the dominant effect. The assumptions of Beer's law indicate that the absorbance should be more linear at the lower absorbances observed at 1100 nm if the effect was due to straight absorbance without scatter.

Figure 23:
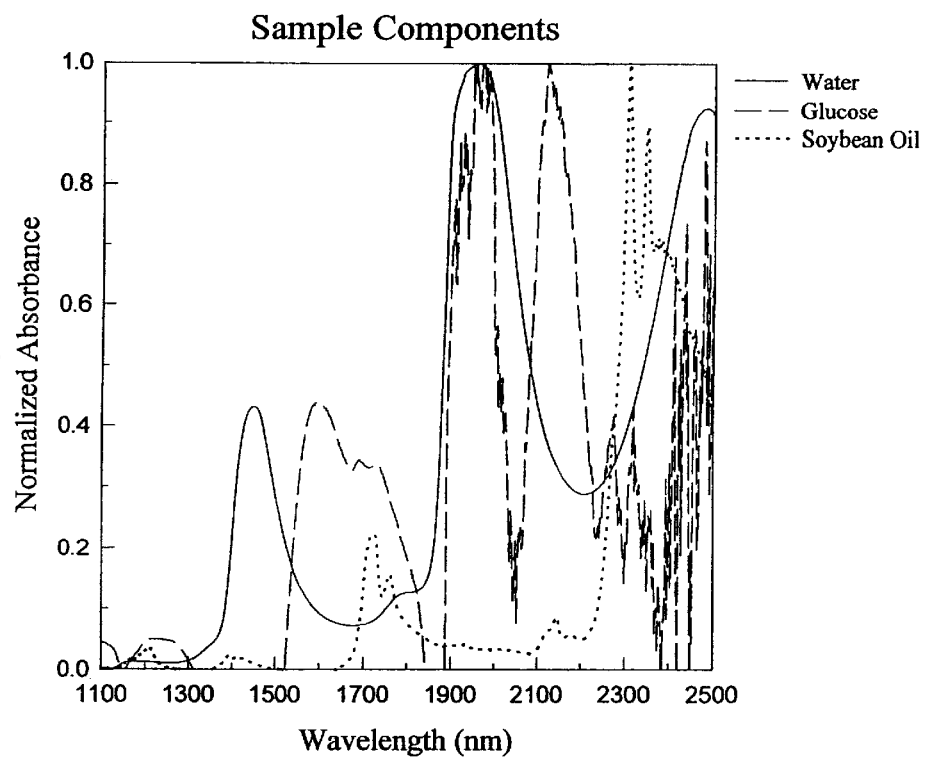
FIG. 23 shows normalized absorbance spectra of water, glucose and soybean oil from 1100 to 2500 nm.

A single spectral range is used for analysis. One aspect of this experiment is to demonstrate the ability or lack of ability of PLS to predict glucose in the presence of a scattering medium. It is not the intent of this experiment to determine the optimal overall processing algorithm in terms of, for example, wavelength selection, MSC, and Fourier Filtering. Algorithm parameters should be revisited if this approach fails or to establish new processing routines. The spectral range chosen is based upon FIG. 23. The spectra range is a combination of 1100 to 1380, 1490 to 1860 and 2050 to 2350 nm. The 1100 to 1380 nm region includes the region that is most dominated by scattering. In the first overtone and combination band spectral regions, the fat absorbance bands strongly interfere with the two of the lowest energy glucose bands. In both regions the fat/oil absorbance bands do not interfere with the high energy, low wavelength, glucose absorbance band. The strongly absorbing fat band spectral regions are included for aid in removing the fat absorbances and the underlying glucose information. The 1490 and 2050 nm limits have been extended to higher frequencies to include the high frequency glucose absorbance bands. The 1860 nm limit is chosen to eliminate the very strong temperature effects and surface water effects observed from 1880 to 1900 nm.

PLS is used to analyze the glucose in Intralipid spectral data set. Initially a crossvalidation analysis is employed. The excluded sample includes all four replicates of the sample. The SEP versus the number of PLS factors is plotted in FIG. 24. A large decrease in the SEP is observed with the fourth PLS factor. The SEP is observed to continue to decrease through 10 PLS factors. A concentration correlation plot is presented in FIG. 25 for the eight PLS factor model which has a SEP of 11.7 mg/dL (0.65 mM). The error of the reference method is 9.2 mg/dL. The predictions are observed to fall evenly above and below the ideal line regardless of the glucose concentration. Typically, the first replicate predicts low and the later replicates predict high. This may be a temperature issue, but has not been further investigated. Further, no correlation between the error in the predicted glucose value and the Intralipid concentration has been found.

Figure 26A:
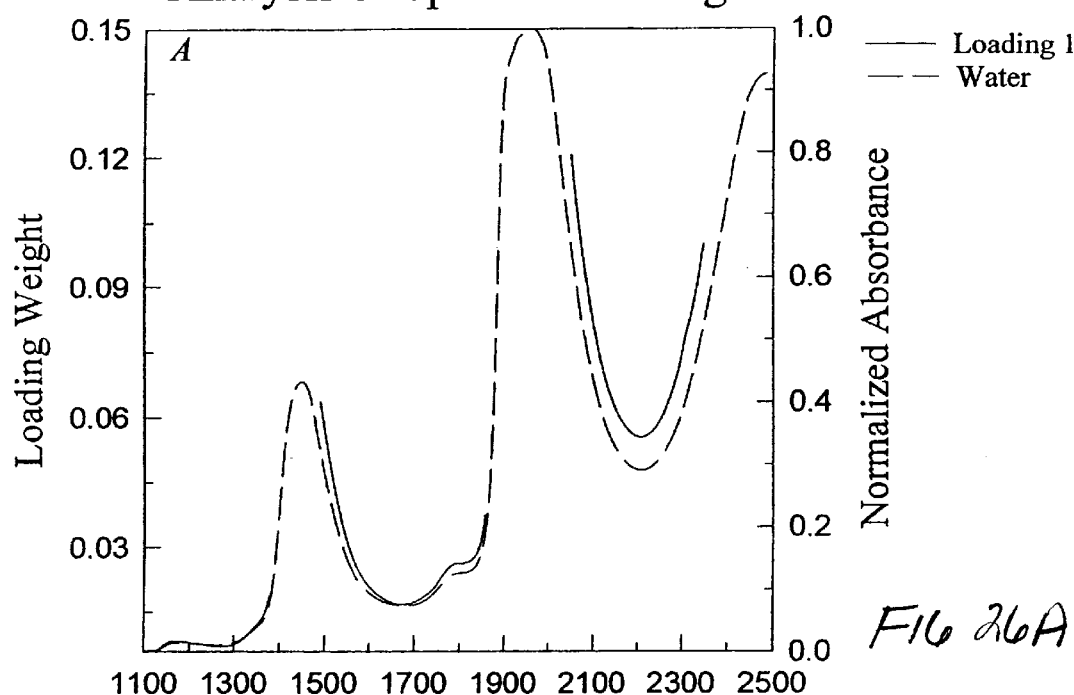
FIG. 26A shows the first spectral loading overlaid with a normalized water absorbance spectrum.
Figure 26B:
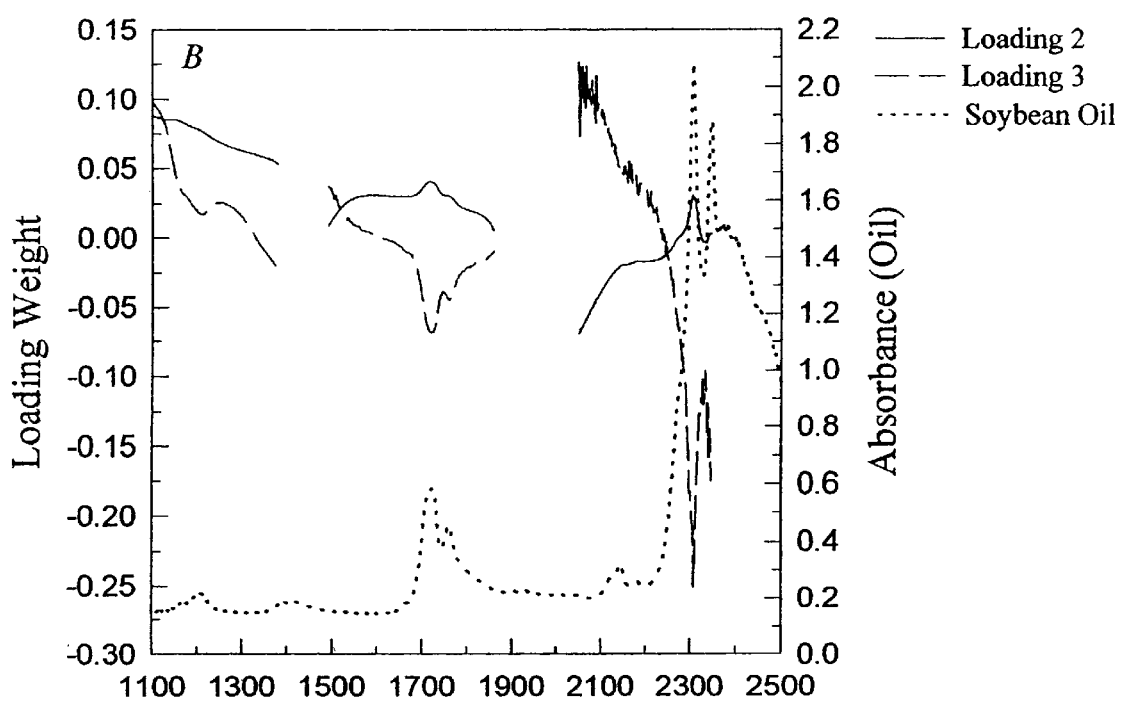
FIG. 26B shows the second and third spectral loading overlaid with a soybean oil absorbance spectrum.
Figure 26C:
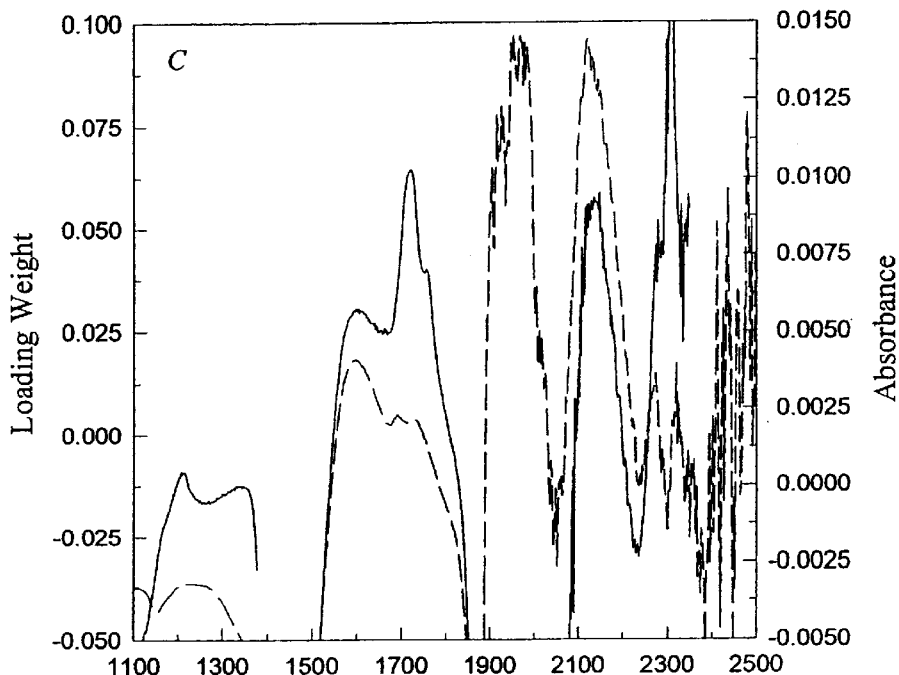
FIG. 26C plots the fourth spectral loading along with a glucose absorbance spectrum.

The spectral loadings of the eight PLS factor model are interpreted in FIGS. 26 A–C. In FIG. 26A, the first spectral loading is plotted along with a normalized water absorbance band collected using a 1 mm transmission cell on the NIRS 5000. The major features of water are all present in the first loading. A frequency dependent difference from the water absorbance band may be due to scattering being more dominant at higher frequencies (lower wavelength). The second and third spectral loading are plotted in FIG. 26B along with and absorbance spectrum of soybean oil collected in transmittance mode on a Nicolet Magna 860. The major absorbance bands of oil located at 2308, 2347, 1760 and 1724 nm are all present in the second and third spectral loadings. The second and third loadings show a frequency dependent drift from 1100 to 1300 nm indicative of the frequency dependence of light scattering. Temperature effects are more difficult to see due to the wavelengths selected. The fourth spectral loading is plotted along with a glucose absorbance spectrum in FIG. 26C. Glucose absorbance bands centered at 1626 and 2105 nm are observed in the spectral loading. Recall that the large drop in the SEP occurred with this factor. The glucose bands at 2272 nm and 2326 nm may be present but are masked by the continued modeling of the fat/oil absorbance bands. The fat bands in the first overtone region are still present in this spectral loading. Additional spectral loadings become increasingly difficult to interpret; however, glucose is observed in the $5^{th}$ and $6^{th}$ loading. Noise begins to dominate in the combination band region by the $7^{th}$ factor but is not limiting by the $8^{th}$ factor in the first and second overtone spectral regions.

Figure 24:
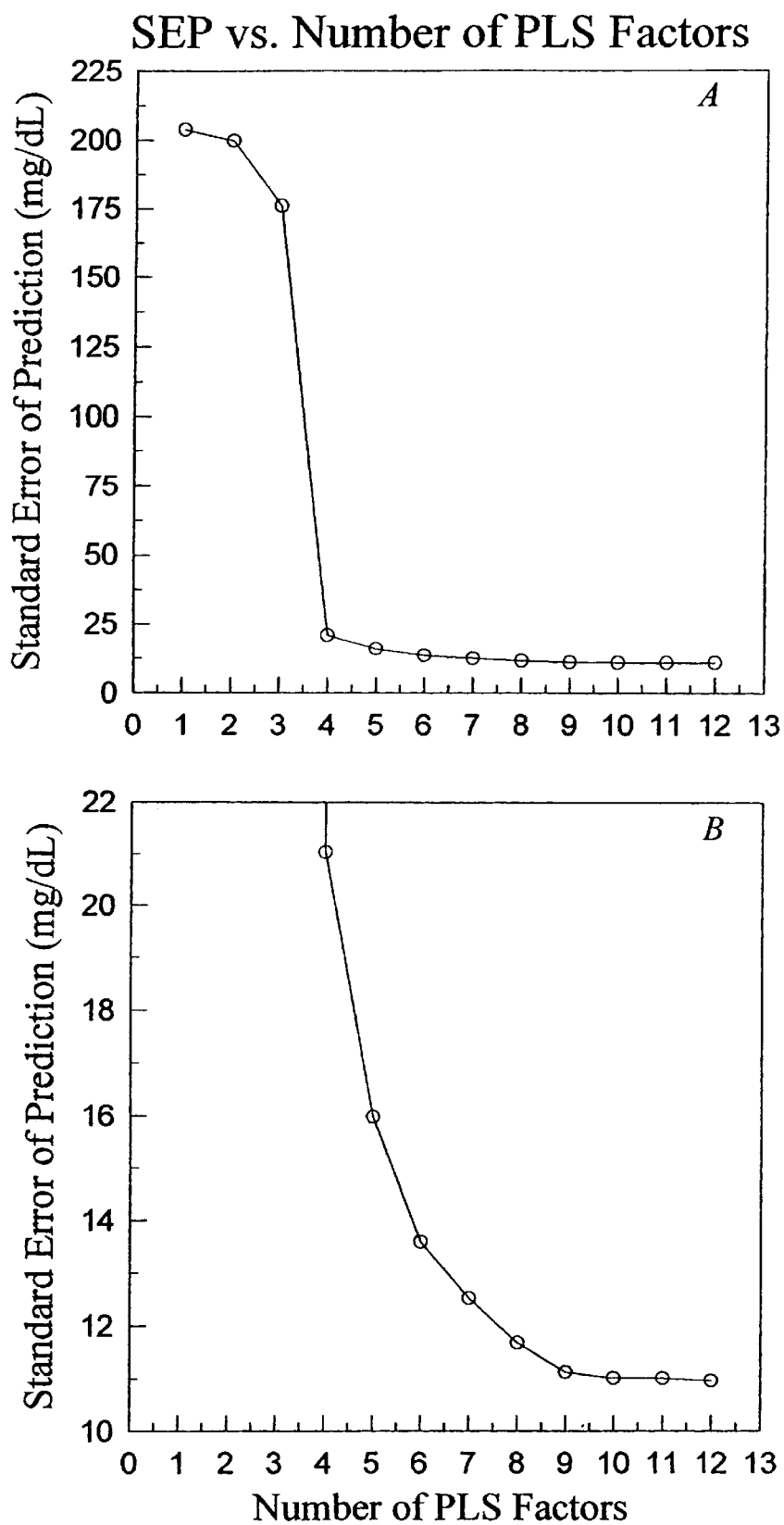
FIG. 24 shows that the standard error of prediction versus the number of PLS factors utilized.
Figure 25:
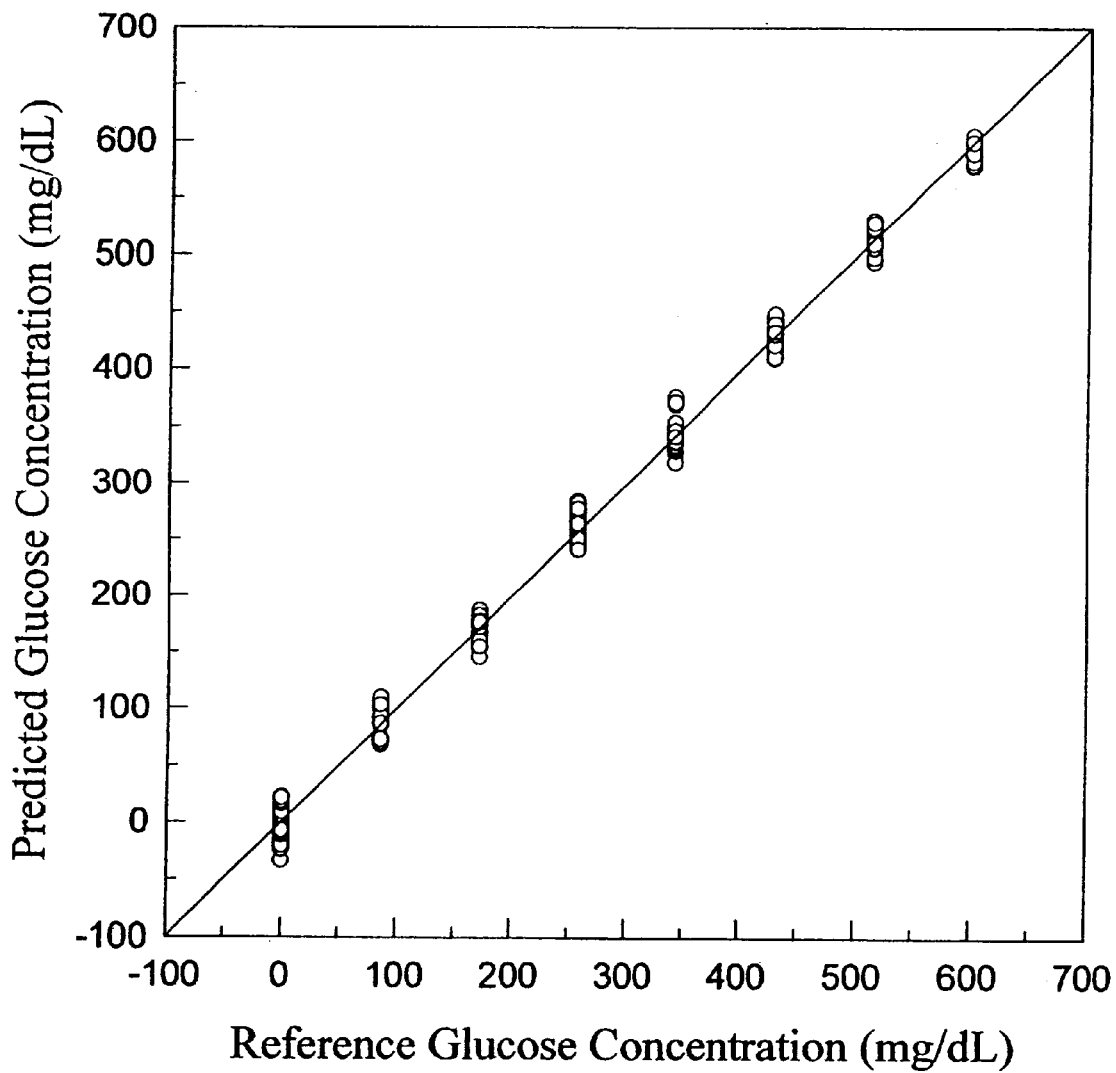
FIG. 25 is a concentration correlation plot for the eight PLS factor model that has a SEP of 11.7 mg/dL (0.65 mM)

The lack of any glucose information in the first three spectral loadings couples well with the poor SEP's determined with the first three factors, see FIG. 24. The large decrease in the SEP with the $4^{th}$ factor is suggested by the appearance of glucose in the $4^{th}$ spectral loading. The continued decrease in the SEP with additional factors is again supported by the information observed in the spectral loadings. The correlation of the SEP and the glucose information observed in the loadings is strong evidence that glucose rather than the displacement of water by glucose is being modeled by PLS.

Study 3: Glucose, Water, Prepared Intralipid in Diffuse Reflectance

Introduction

Study 3 extends Study 2 by collecting a glucose, water and modified Intralipid data set in diffuse reflectance mode on a modified NIRS-5000. Again the glucose concentrations and glycerol free Intralipid concentrations are random versus each other and time. This study is a building block to demonstrate that glucose may be measured in diffuse reflectance mode in a tissue phantom before basis set components such as albumin and urea are added to the matrix.

Experimental

Sixty-four chemically unique samples were prepared with glucose concentrations ranging from 0 to 600 mg/dL and modified Intralipid concentrations ranging from 5 to 10%. Stock solutions of 5142 mg/dL glucose, 10% Intralipid prepared without glycerol and DI water were used to prepare the samples.

The samples were collected using an NIRS-5000 reflectance spectrometer configured with four PbS detectors, two silicon detectors and a sapphire window without AR coating. A total of 64 scans per sample were collected 1100 to 2500 nm. Samples were placed in an infinite pathlength aquarium based cell with a sapphire bottom holding 14 mL of sample. A 99.9% reflective spectralon standard, fitted to the instrument window, was used as a reference. A reference was collected immediately prior to the four sample replicates.

Results and Discussion

Instrumental and sample errors existed in this study and were known prior to its execution. One such error was the presence of specular reflectance. The specular reflectance occurred multiple times as the light traveled into and out of the sample. It occurred as the light reached the instrument sample cell windows both when the light was moving to the sample and as it was reflected back towards the detectors. The specular reflectance makes analysis of the data extremely difficult. In spite of these instrumental concerns, this data set provides an excellent building block for future experiments.

The NIRS instrument was very warm to the touch. As a result the samples were heated throughout the analysis. Temperature variations between sample replicates resulted from heating by the instrument. Another instrument issue is the fact that the NIRS uses a small linear range and due to the noise of the system the data had a poor signal to noise ratio.

The largest sample error was the existence of an inverse relationship between glucose and Intralipid concentrations and glucose and water concentrations. Because the samples were prepared volumetrically from stock solutions the concentration of the glucose depends on dilution by the Intralipid and DI water stocks. This problem is inherent in a three constituent system.

The combined instrumental issues led to standard errors of prediction that indicate that glucose is being modeled. However, since glucose inversely correlates with water and the spectral loadings were difficult to interpret the extent to which PLS utilizes the glucose information and the inverse correlation could not be established. The prediction results which are similar to Study 2 merely indicates the ability to determine glucose in diffuse reflectance mode in a scattering medium. In order to separate out the glucose information from the inverse correlation affects, the interfering compounds of urea and albumin are added in subsequent studies. Addition of the large molecular weight albumin has the additional benefit of lowering the water concentration so that the body is more closely modeled.

Study 4: Glucose, Urea, Water and Intralipid in Diffuse Reflectance with Inverted Praying Mantis Accessory Introduction This study was the second in a series of studies designed to measure glucose in a diffuse reflectance medium that models the body spectrally. Spectra were collected of samples consisting of glucose, water, urea and modified Intralipid using a Nicolet 860 spectrometer with a customized PIKE inverted praying mantis accessory. Addition of urea in the experimental design helps to break the inverse correlation between water and glucose. The most important remaining issue is the existence of a sapphire window on the bottom of the aquarium based sample cell analyzed by the inverted praying mantis accessory, which leads to specular reflectance. The use of the Nicolet spectrometer minimizes the large temperature affects observed in Study 3.

Experimental

A total of 114 chemically unique samples were prepared with 0 to 600 mg/dL glucose, 0 to 521 mg/dL urea, 10 to 15% modified Intralipid and DI water. Samples were scanned using the Nicolet 860 spectrometer with the PIKE (Madison, Wis.) inverted praying mantis accessory. Samples were placed in a sample cell simulating infinite pathlength, with an AR coated sapphire bottom.

Results and Discussion

The Nicolet and PIKE accessory were not warm to the touch and did not cause the samples to heat during analysis and therefore this problem was eliminated.

The Nicolet data had lower noise than the NIRS data and so the S/N was improved. Also, the Nicolet has a greater linear range than the NIRS.

The inverse relationship between glucose and Intralipid and glucose and water concentrations was not present in this study due to the addition of urea to the samples. However, there still is an inverse relationship between the glucose concentration and the sum of the remaining constituent concentrations. Also, there were no interferences in the $1^{st}$ Overtone region limiting the ability to perform resolution studies. The addition of albumin to the samples would help to improve upon both of these issues.

An issue unique to this study was the concentration range of the Intralipid. The range used is higher than that which models noninvasive scans spectrally and thus the fat bands are more dominant than would be seen in a noninvasive scan. This was done to increase the scattering in order to increase the S/N levels in the combination band region.

Using single beam spectra, and a leave 20 out cross validation yielded glucose standard fitting errors of calibration of 11.29 mg/dL and standard prediction errors of 14.71 mg/dL using the $2^{nd}$ overtone, $1^{st}$ overtone and combination band region. These results were obtained using a PLS model with twenty principle component scores.

The issues of specular reflectance is removed in Study 5 and an additional interfering substance, albumin, is added.

Study 5: Water, Modified Intralipid, Albumin, Urea and Glucose Using Diffuse Reflectance Based Fiber Optic Spectrometer Introduction Noninvasive determinations of glucose have been performed with near-IR light in diffuse reflectance mode. Unfortunately, interpretation of multivariate analysis of glucose determinations from simple glucose tolerance tests is hindered by co-variation of analytes, knowledge of depth of penetration, knowledge of total pathlength and changes in the scattering coefficient among other concerns. Due to these issues, a class of samples that act as tissue phantoms has been developed and is collectively known as Intra-serum. Spectra of Intra-serum solutions model spectra of skin. Analysis of data sets of spectra of Intra-serum samples collectively lead to insight into issues associated with noninvasive glucose determinations based upon diffuse reflectance based near-IR analysis. Study 5 focuses on the experimental design of the latest Intra-Serum studies that are referred to here as the Intra-Serum 1 and Intra-Serum 2 studies.

To demonstrate glucose determinations in diffuse reflectance mode and to provide specific instrumentation specifications, a diffuse reflectance medium was required with certain parameters. Chief among the requirements for the prepared samples is that the sample may be scanned in diffuse reflectance mode with no specular reflectance being detected. An additional requirement is that all absorbing components of the prepared sample are a subset of major absorbers of the body in the skin in the near-IR region. A third requirement is that all major absorbance bands present in the body be present in the samples. Finally, a family of samples needs to be created in which the concentrations of all individual components of the sample are quantitatively known and that they may be analytically varied such that as a class each analyte is random in concentration versus the other analytes.

The development of a family of samples, known collectively as the Intralipid studies, has progressed through multiple stages. In each stage, the complexity of the sample has been increased and instrumental limitations have decreased.

In the initial studies, the samples consisted of glucose, water and Intralipid. These studies were run on an NIRS. Several major issues existed including large temperature transients in the sample during analysis, specular reflectance, poor S/N and a small linear range in absorbance. However, the chief problem was that the glucose concentration and the water concentration were inversely related. This means that as the glucose concentration was increased, the water concentration decreased. Because multivariate analysis cannot distinguish the spectral variations due to an increase in glucose or a decrease in water, the relative contribution of the glucose absorbance band and the decrease in the large water absorbance band to the SEP were difficult to quantify.

In later studies, changes in instrumentation and in sample preparation greatly reduced many of the major issues of the glucose, water and Intralipid NIRS studies. The use of the Nicolet with a customized PIKE inverted praying mantis accessory (Madison, Wis.) resulted in lower noise levels and hence larger S/N levels. The large temperature effects due to the placement of the sample on the very warm NIRS were eliminated. The Nicolet's inherent linear range in absorbance is greater than the NIRS, thereby minimizing that issue. In addition to instrument changes, the sample preparation was improved with urea being added to the sample in addition to water, modified Intralipid and glucose. This allowed an experimental design to be implemented in which the glucose concentrations are random versus the concentrations of all of the other analytes and versus time. However, several major issues still existed. As used, the praying mantis accessory yielded spectra with significant specular reflectance greatly hindering analysis. In addition, glucose determinations in the $2^{nd}$ overtone region were still inconclusive as glucose could be determined as the total sample minus water, modified Intralipid and urea. The addition of urea greatly improved confidence in $2^{nd}$ overtone glucose determinations, but the presence of additional analytes would further increase confidence. Finally, generation of a resolution specification in the $1^{st}$ overtone region was complicated by the fact no interferences were present in the 1500 to 1650 nm region where glucose has a large absorbance band and urea does not absorb.

In the Intra-Serum 1 and Intra-Serum 2 studies, continued improvements in instrumentation, sample preparation and experimental design have culminated in a data set that allows a strong demonstration of glucose determination in diffuse reflectance in each of the $2^{nd}$ overtone, $1^{st}$ overtone and combination band spectral regions. In addition, the data set is of high enough quality for additional analysis such as resolution effects, net analyte signal determinations and noise analysis.

Experimental
Instrumentation

Two studies were run (Intra-serum 1 and Intra-serum 2), each with its own instrument configuration and spectral range which are summarized below.

In both studies, spectra were collected using a modified Nicolet Magna 860 (Madison, Wis.) spectrometer. The Intra-serum 1 data set utilized an Oriel model #66187 (Stratford, Conn.) auxiliary source, which was mechanically modified to couple into a Magna 860. The 600 W Oriel source was replaced with an L7390A, 100 W Gilway (Woburn, Mass.) tungsten-halogen source. A 2" diameter quartz piano-convex lens collimated the light, which was delivered into the Michelson interferometer of the Magna 860. The Intra-serum 2 data set utilized a customized auxiliary source accessory (ARA Engineering, Mesa, Ariz.). The Gilway source was again utilized. A spherical concave backreflector with a 35 mm radius of curvature, 51.0 mm diameter and 17.5 mm focal length was employed. A gold plated, 38.1 mm focal length, 76.2 axial displacement off-axis parabolic reflector was used to collect the light and collimate it through the Michelson interferometer. An anti-reflective (AR) coated 1.075 and 1.450 $\mu$m longpass filter was employed between the source and the Michelson interferometer in the Intra-serum 1 and Intra-serum 2 studies, respectively. In both studies, the bench was configured with a $CaF_2$ beamsplifter. A 1" diameter, 1" focal length sapphire lens, AR coated on both sides, positioned in the sample compartment coupled light into a custom-made 1 meter bifurcated fiber optic bundle (Collimated Holes, Campbell, Calif.).

The fiber bundle consists of 261 close-packed, ultra low -OH 200 $\mu$m diameter silica input fibers with 240 $\mu$m silica cladding and 280 $\mu$m polyimide buffer configured in a rectangle. The sample interface is a rectangle of 37 fibers by 9 fibers. The reference standard was a 2% and 5% Labsphere diffuse reflectance standard in the Intra-serum 1 and Intra-serum 2 studies, respectively. The fiber bundle was inverted into a sample container with greater than 10 mm of Intra-serum in all directions from the fiber bundle tip. A total of 72 detection fibers are evenly intercalated within the excitation fibers. Collected light was focused through two 10 mm diameter, 10 mm focal length sapphire lenses, which were AR coated on both sides, into a 2.6 $\mu$m 3-stage TE cooled InGaAs detector operated at 7.375±0.125 k$\Omega$ (−19° C.). An OPA-627BM operational amplifier (Burr Brown) was utilized in the first gain stage of a preamplifier board which coupled into the Nicolet amplifier board. The operational amplifier was configured with a 0.604 M$\Omega$ and 2.72 M$\Omega$ resistor in the Intra-serum 1 and Intra-serum 2 studies, respectively. The low pass filter capacitor was set at 5.5 kHz and the high pass filter was maintained at 1.5 kHz. The Nicolet was purged at a rate of 25 CFM and 25 psi with dried and oil free air from a Balston 75-62 FT-IR air purifier.

In both the Intra-serum land Intra-serum 2 studies, the sample was scanned in diffuse reflectance mode in a sample cell designed to yield total external light blocking and a sample equivalent to one of infinite size. Each sample was raised on a lab jack until the fiber optic probe penetrated 10 mm into the sample. This allows the fiber optic probe to remain stationary during the course of the experiment. Contact of the fiber with the Intralipid led to light blocking to the noise level of the A/D by the large water absorbance band at 1.95 $\mu$m. A total of 22 mm of sample exists between the tip of the fiber probe and the sample holder. This results in a sample with an infinite depth.

Stock Solutions

Three stock solutions were analytically prepared with reagent grade Fisher Scientific (Pittsburgh, Pa.) chemicals: 4500 mg/dL 99.9% D-glucose, 624.99 mg/dL reagent grade urea and 10000.04 mg/dL bovine serum albumin Fraction V. Each of these three stocks was prepared with 0.483 g/L 5-fluorouracil. A fourth stock of 30% Intralipid was prepared by Fresenius Kabi (West Clayton, N.C.) without glycerol and was separated at time of preparation into 100, 100 mL intravenous bottles. A fifth stock of mega pure de-ionized water was generated as needed throughout the experiment.

Sample Preparation

Using the stock solutions, a total of 102 samples were prepared in the Intra-serum 1 data set. Glucose concentrations ranged from 38.84 to 598.1 mg/dL, modified Intralipid from 2.99 to 8.00% by mass, urea from 4.80 to 69.78 mg/dL and albumin from 492.7 to 2005 mg/dL. In Intra-serum 2, a total of 152 samples were prepared. Glucose concentrations ranged from 38.20 to 601.5 mg/dL, modified Intralipid from 2.98 to 8.02%, urea from 4.81 to 70.4 mg/dL and albumin from 494 to 2013 mg/dL. The samples were prepared such that the concentrations of each component (glucose, Intralipid, urea, albumin and water) were randomly correlated between samples. The samples were prepared gravimetrically using a micropipette to transfer varying amounts of each constituent's stock solution dropwise into a sample container of which the mass was recorded after the addition of each stock. Sample concentrations were later calculated using the density of each solution. The order of addition of the stock was glucose, Intralipid, urea, albumin and de-ionized water.

Software

In the Intra-serum 1 data set, the Nicolet software was configured to collect single beam spectra from 11,000 to 3500 cm$^{-1}$(0.909 to 2.857 μm) at 4 cm$^{-1}$(0.3 to 3.2 nm) resolution. In the Intra-serum 2 data set, the Nicolet software was configured to collect single beam spectra from 7,500 to 3,500 cm$^{-1}$(1.333 to 2.857 μm) at 4 cm$^{-1}$(0.7 to 3.2 nm) resolution. For each sample in both studies, a total of 16 replicates with 128 co-added spectra per replicate were collected with a gain setting of 1. Reference spectra were collected immediately prior to and after each sample. Spectra were triangularly apodized, Mertz phase corrected, treated with no zero filling, collected with a sample spacing of 1.0 and subjected to an 11000 Hz digital low-pass filter and a 200 Hz digital high-pass filter.

Procedures

All subsequent processing of these data sets was performed using Matlab 5.2. Absorbance spectra were generated using the mean reference single beam spectrum. In each data set, the data was divided into calibration and prediction data sets. For the Intra-serum 1 data set, 12 samples fell out of the 95% confidence limit of a one-sided statistical f-test based upon the first five principal component scores and were removed. In the Intra-serum 2 data set, 8 samples were removed due to obvious specular reflectance. Unless otherwise stated, all 16 replicate sample spectra were co-added prior to analysis. Multiplicative scatter correction was performed on the entire spectral range, followed by a 61 point Savitsky-Golay smoothing algorithm prior to wavelength selection. A 51 point smoothing algorithm was employed for the combination band region on the Intra-serum 2 data set. In the Intra-serum 1 and 2 data sets, the independent prediction set consisted of the last 25 and 20% of the samples, respectively. Model parameters were generated using the calibration data set with a leave one sample out crossvalidation procedure.

Results and Discussion

Experimental Design

The experimental design consisted of forming a 4-dimensional data cube with the axis being defined by the desired concentrations of the modified Intralipid, albumin, urea and glucose. The cube was subdivided into 108 sub-cubes. One sample was prepared for each sub-cube with the concentrations of each constituent being randomized within each sub-cube. Finally, spectra of the resulting samples are collected in a random order versus time. This process ensures that the glucose concentration and the concentrations of all additional sample constituents are random versus time. Again, this random variation is designed into the data sets due to the inability of multivariate analysis techniques to separate causes of spectral variation. The correlation coefficient of each Intra-serum constituent versus sample number (time) and versus all other sample constituents are summarized in Table 2. All correlation coefficients are below 0.1 indicating extremely poor correlations between analytes.

This random variation is designed into the data set due to the inability of multivariate analysis techniques to separate causes of spectral variation. This is required as some instrument parameters may change systematically throughout the course of the experiment. An example is that the auxiliary source caused the spectrometer base plate temperature to increase throughout the experiment. If glucose concentrations were run in ascending order, then PLS would not have been able to distinguish between the glucose analyte variations and any optical throughput changes that occur due to the increased base plate temperature. The extent to which PLS then uses the change in light throughput to predict the glucose concentrations would then be difficult to quantify.

TABLE 2

Correlation Coefficients of each Sample Constituent with Time and all other Constituents.

| Intra-serum 1 Intra-serum 2 | Time | Intralipid | Albumin | Urea | Glucose |
|---|---|---|---|---|---|
| Time | N/A | −0.0463 | 0.0054 | −0.0354 | −0.0013 |
|  |  | 0.0133 | 0.0411 | −0.0301 | −0.0334 |
| Intralipid | −0.0463 | N/A | −0.0519 | −0.0376 | 0.0637 |
|  | 0.0133 |  | 0.0804 | 0.0629 | −0.0031 |
| Albumin | 0.0054 | −0.0519 | N/A | −0.0014 | 0.0076 |
|  | 0.0411 | 0.0804 |  | −0.0193 | 0.0311 |
| Urea | −0.0354 | −0.0376 | −0.0014 | N/A | −0.0979 |
|  | −0.0301 | 0.0629 | −0.0193 |  | 0.0212 |
| Glucose | −0.0013 | 0.0637 | 0.0076 | −0.0979 | N/A |
|  | −0.0334 | −0.0031 | 0.0311 | 0.0212 |  |

The data sets were primarily designed to demonstrate the ability to measure glucose in diffuse reflectance mode. This requires that the glucose concentrations are random versus time. Conclusive multivariate analysis also requires that the concentration of glucose is random versus the concentrations of all other analytes. Both of these requirements are demonstrated below.

The data sets were also designed to bring insight into the issue of resolution. In an FT system, as resolution is degraded, the retardation of the movable mirror within the Michelson interferometer is reduced. This requires a shorter time period per scan. Therefore, at poorer resolutions a larger number of scans may be collected and averaged to reduce spectral noise. To compare spectra collected at different resolutions, compensation must be made for the additional signal averaging that could have been performed for the spectra collected at degraded resolutions. To allow this comparison, all sixteen replicates of each sample were collected without removing the sample from the sample holder. A single set of replicate scans is then used to represent spectra collected at higher resolution. As the resolution is degraded, more spectra can be collected in the time required for the spectra collected at high resolution. Therefore, additional replicates are averaged to compensate for this tradeoff.

Instrumentation/Spectra Characterization

A modified Nicolet 860 Fourier transform based spectrometer is utilized in these studies. A customized auxiliary source is optically coupled to a customized fiber optic interface, which in turn is coupled to the sample. Combined these allow a high throughput, high resolution, low noise and fast data acquisition spectrometer. The fiber bundle eliminated the specular reflectance term.

Figure 27:
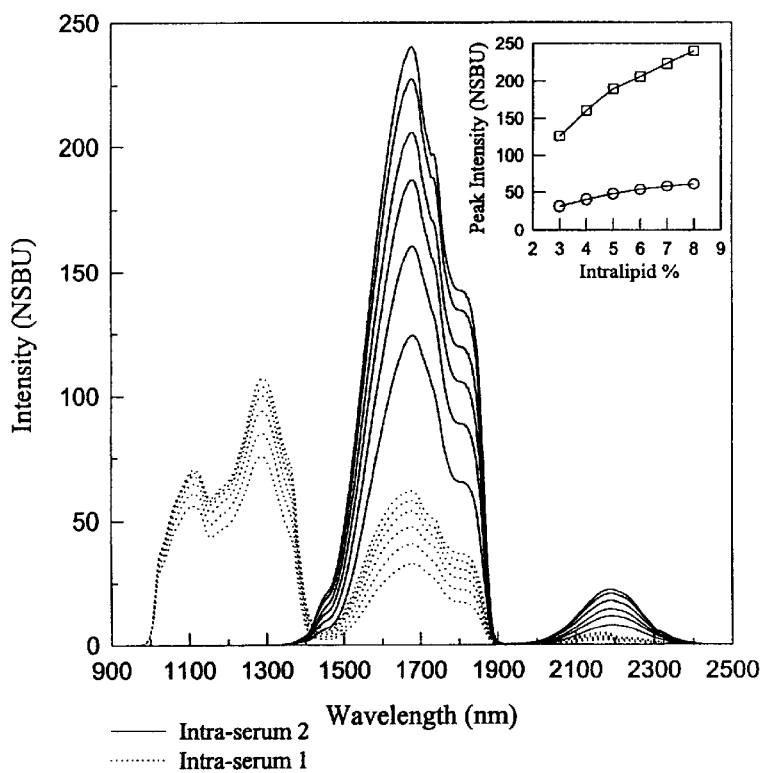
FIG. 27 shows representative single beam spectra from the Intra-serum 1 and Intraserum 2 data sets.

Representative single beam spectra of 3, 4, 5, 6, 7 and 8% Intra-serum samples from the Intra-serum 1 and Intra-serum 2 data sets are presented in FIG. 27. Use of the 1450 nm longpass filter eliminated signal in the 2$^{nd}$ overtone region in the Intra-serum 2 data set, which allows the dynamic range of the Nicolet to be freed for the detection of signal in the $1^{st}$ overtone and combination band regions. As the dynamic range was filled in each study, an increase in peak intensity in the $1^{st}$ overtone region of 382% is observed and in the combination band regions an increase in the peak intensity of 524% is observed. The larger gain in the combination band region is due to the removal of the quartz optic in the auxiliary source. The inset shows the peak $1^{st}$ overtone intensity for the six Intra-serum samples at 1678 nm. The nonlinear nature is expected in a scattering medium and will lead to additional factors being required with the linear PLS analyses that follow. The elimination of specular reflectance is demonstrated at 2000 nm where the water absorbance is high.

A criterion for interpretation of near-IR glucose analysis is the spectrometer noise level. The noise levels are generated for each study according to $$Noise_{(absorbance)} = 0.4343 \cdot \sqrt{\frac{\sigma_R^2}{I_S^2}}$$

(J. Ingle, S. Crouch, *Applied Optics*, pp. 548 (1988)). Noise is estimated as the root mean square of successive reference spectra collected throughout the studies. The intensity is the mean single beam spectrum in each of the Intra-serum studies. As expected, the resulting noise levels are proportional to the absorbance of water, though the diminished light throughput affects of fat and the quartz optic in the Intra-serum 1 study may be observed. The instrumentation utilized in the Intra-serum 2 study yields lower noise levels as is expected from the increased signal levels made possible with the 1.450 $\mu$m longpass filter. Noise levels of less than 10 micro-absorbance units are generated in the second overtone and $1^{st}$ overtone regions. In the combination band region, noise levels increase towards 100 micro-absorbance units. While net analyte signal calculations are beyond the scope of this paper, after adjusting for the net pathlength as a function of frequency these noise levels are on the order of the signal level for glucose in the $1^{st}$ and $2^{nd}$ overtone regions and are restrictive in the combination band region.

Multivariate Analysis

Throughout the rest of this report, analysis will be performed on 3 spectral regions or combinations of these regions: the combination band region (2025 to 2375 nm), the $1^{st}$ overtone region (1500 to 1840 nm) and the $2^{nd}$ overtone region (1025 to 1400 nm). Each of the regions contains glucose absorbance bands, but no attempt is made to further optimize these ranges in terms of glucose predictions. The extremes of each region are based upon the absorbances of the interfering analytes. For example the 2025 nm limit is designed to include the protein absorbance band at 2050 nm, the 1400 and 2375 nm limits are based upon water absorbance leading to high noise levels at longer wavelengths and the 1840 nm limit is due to free water and temperature affects at 1890 nm.

The literature points out that, with the glucose profiles utilized in some studies, multivariate techniques may model instrument variations correlating to the actual glucose levels with prediction errors equivalent to the glucose errors reported (M. Arnold, J. Burmeister, G. Small, *Analytical Chemistry*, vol. 70, pp. 1773–1781 (1998)). In the studies reported here, in order to determine if any instrument variation is modeled by PLS, the reference spectra collected with each sample are utilized in place of the sample spectra with the same preprocessing and spectral ranges as used to determine glucose. For each spectral range analyzed, results in Table 3 show prediction errors of roughly 155 and 177 mg/dL are achieved for the Intra-serum 1 and 2 data sets, respectively. The standard deviations of the actual glucose values in the prediction data sets are 156.5 and 178.8 for the two data sets, respectively. The resulting f-test values indicate that the reference spectra can not be used to determine the glucose concentrations at the 90% confidence level ($F_{90}$=1.70). These tests on the reference spectra clearly demonstrate that variations in the spectrometer are not being utilized to determine the glucose concentrations. However, it should be pointed out that this test does not address systematic changes in the sample.

Subsequently to the f-test, a PLS analysis is utilized on the preprocessed data for the Intra-serum 1 and 2 data sets for each of the spectral regions, Table 3. Notably, glucose predictions are achieved independently in each of the $2^{nd}$ overtone, $1^{st}$ overtone and combination band spectral regions. The $2^{nd}$ overtone and combination band region yield glucose predictions of 40 mg/dL which are significant at the 99.9% confidence level ($F_{99,9}$=3.74). The data in Table 3 indicates that the primary glucose information is in the first overtone spectral region. Combining the combination band region and $1^{st}$ overtone region failed to reduce the SEP of glucose in the Intra-serum 2 data set. This may be due to the high noise levels observed in the combination band region. However, combining the $2^{nd}$ overtone region to the $1^{st}$ overtone region led to a 50% reduction in the SEP in the Intra-serum 1 data set.

For the $1^{st}$ overtone Intra-serum 2 model, the standard error of the calibration, monitoring and independent prediction sets are plotted against the number of PLS factors, FIG. 28A. A classic decrease in error with the initial factors is observed. In addition, the monitoring and prediction errors closely track those of the calibration model. The concentration correlation plot for the 17 factor model is presented in FIG. 28B. No bias is observed versus the reference method. As with all models examined herein, the error does not increase at lower glucose concentrations indicating that random noise is not the limiting criterion for glucose determination in these data sets. This agrees well with the significantly larger single beam intensity in the first overtone region of the Intra-serum 2 data set does not lead to a minor reduction in the resulting SEP.

Figure 28:
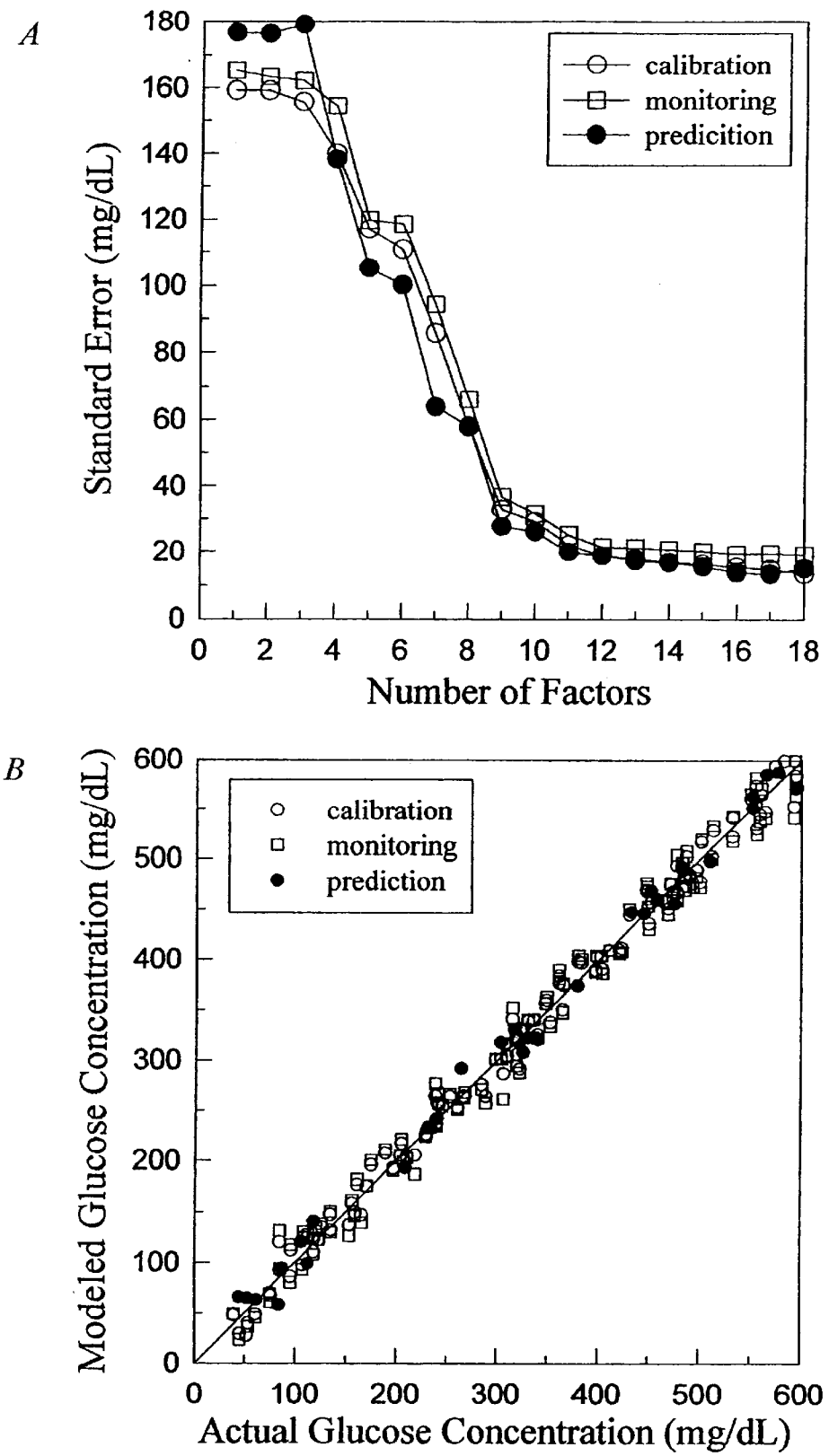
FIG. 28A shows the standard error of calibration, monitoring and prediction versus the number of PLS factors utilized in the model and 28B shows the corresponding concentration correlation plot.
Figure 29:
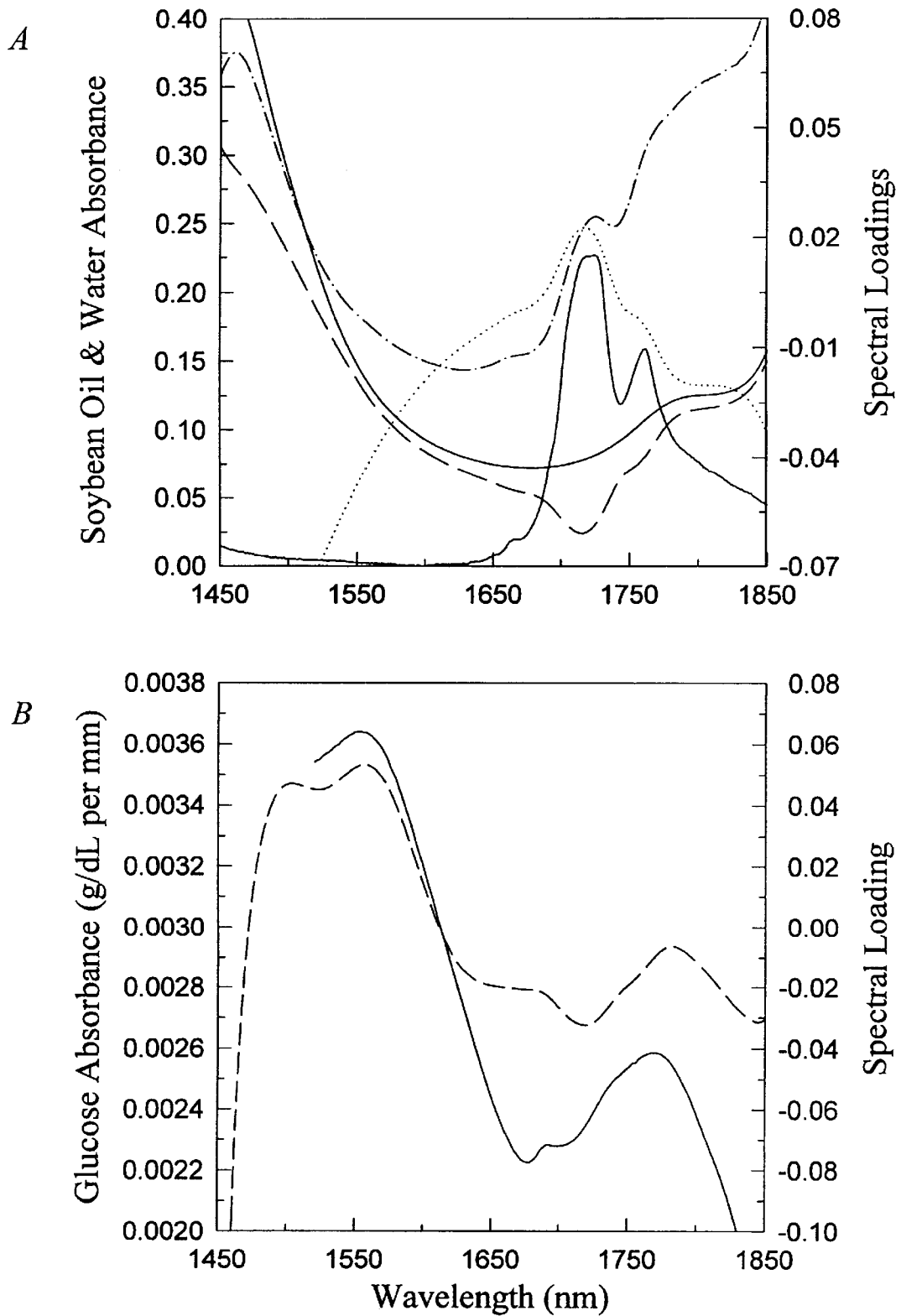
FIG. 29A shows the first three spectral loadings ––– loading 1, ······ loading 2, —·— loading 3) overlaid with water —— and soybean oil —— absorbance spectra and 29B shows the fourth spectral loading - - - overlaid with a glucose ––– absorbance spectrum.

For the model presented in FIG. 28, the first four spectral loadings are examined in FIG. 29. The first three loadings show strong correlations with water and soybean oil absorption bands. No peaks in the first three loadings correspond to glucose absorbance bands. This is consistent with the standard error of the calibration, monitoring and prediction set being roughly the standard deviation of the glucose values in the model. However, the fourth loading has a peak at 1556 nm that correlates strongly with the glucose absorbance band at 1554 nm. The fourth factor shows a corresponding decrease in the SEP of glucose, which adds confidence to the model. Later factors become increasingly difficult to interpret.

TABLE 3

SEC, SEP and RMS noise levels for Intra-Serum 1 and Intra-Serum 2.

| | Intra-Serum 1 | | | | | | Intra-Serum 2 | | | | | |
|---|---|---|---|---|---|---|---|---|---|---|---|---|
| Spectral Range | SEP Using Ref | f-test Ref | SEC | SEP | # of PLS Factors | f-test Samples | SEP Using Ref | f-test Ref | SEC | SEP | # of PLS Factors | f-test Samples |
| 2$^{nd}$ Overtone | 156.3 | 1.00 | 20.8 | 40.0 | 22 | 15.3 | N/A | | N/A | N/A | N/A | N/A |
| 1$^{st}$ Overtone | 155.0 | 1.02 | 19.3 | 22.1 | 13 | 50.1 | 178.3 | 1.00 | 14.9 | 13.5 | 17 | 174 |
| Combination | 156.1 | 1.00 | 37.1 | 40.4 | 10 | 15.0 | 176.8 | 1.01 | 29.1 | 29.6 | 13 | 36.1 |
| All | 153.9 | 1.03 | 8.83 | 11.7 | 22 | 179 | 177.5 | 1.00 | 11.3 | 13.6 | 21 | 171 |

Conclusions

A family of samples is generated with absorption and reduced scattering coefficients closely matching skin tissue. Additional sample components that represent all of the major near-IR absorbers present in skin are independently added to the matrix. The experimental design utilizes the additional interferences to break all correlations of glucose concentration with the concentrations of all other sample constituents and with time. An f-test utilizing references collected with the spectra demonstrate that subsequent multivariate analyses are not modeling environmental affects on the spectrometer. Multivariate analyses demonstrate successful diffuse reflectance measurements of glucose in each of the three spectral regions (combination band, 1$^{st}$ overtone and second overtone) where glucose is demonstrated to absorb in the near-IR. The results are supported with interpretations of spectral loadings and noise levels.

An Alternative Embodiment of the Invention

An alternative embodiment of the Intra-serum invention is the Intra-gel invention. The Intra-gel samples are Intra-serum samples that have been crosslinked with a suitable crosslinker such as collagen (gelatin). The Intra-gel family of samples retain all of the advantages of the Intra-serum family of samples. In particular, the samples are made entirely out of major near-IR absorbers present in skin in the human forearm. In addition, all of the basis set major near-IR absorbers present in skin may be incorporated into the Intra-gel samples. Each of the components of the gel samples may be individually varied in concentration in a quantitative fashion. The scattering and absorption coefficients of the Intra-gel samples match those of the arm.

The Intra-gel family of samples has additional advantages.

First, the crosslinking allows the water concentration of the samples to be brought down into the 65–75% range matching that of the body. The collagen used as the crosslinking agent again is naturally present in a crosslinked form in skin. Collagen, which is a mixture of alanine and glycine, has near-IR absorbance bands that closely match albumin and globulin.

Second, the crosslinking results in a stable sample that may be used as a standard in diffuse reflectance, transflectance or transmission mode. The Intra-gel samples have the additional advantage of being solids. Therefore, layers of varying thickness may be prepared and stacked. In this way, varying layers of the skin may be simulated with varying layers of Intra-gel samples. In particular, each layer of skin has its own unique chemical makeup. The concentrations of the analytes of interest and interfering compounds may be matched in the stacked Intra-gel samples. In addition, each layer of skin has its own thickness that may be matched or varied with Intra-gel samples. Each layer of skin also has its own index of refraction and particle size distribution that may be matched with the Intra-gel samples. The resulting samples are flexible in each analytes concentration and match the skin layers of the body in terms of reduced scattering and absorbance coefficients, $\mu'_s$ and $\mu_a$ resulting in excellent tissue phantoms. Those skilled in the art will recognize that the disclosure herein enables one to modify these Intra-gel samples to match additional tissues and internal organs in the body.

The first implementation of the Intra-gel studies contained water, collagen, albumin, globulin, soybean oil, lecithin, urea and glucose representing most of the organic basis set components. The concentration range of each component is summarized in Table 4.

TABLE 4

Intra-gel constituents and concentrations

| Analyte | Concentration Range (mg/dL) |
|---|---|
| Albumin | 500–2000 |
| Globulin | 500–2000 |
| Intralipid (soybean oil) | 5–15% |
| Urea | 0–200 |
| Glucose | 0–600 |

The albumin concentration is intentionally lower than physiological concentrations. If albumin concentrations are larger than globulin, then albumin necessarily inversely correlates with the water concentration. This means that albumin may be measured by multivariate techniques such as PLS in spectral regions where it does not absorb. In published serum studies, albumin and globulin were determined. However, globulin is measured by determining the total protein and subtracting the globulin protein level. The correlation between total protein and the similarity of absorbance between albumin and globulin introduces some doubt in the protein determination. In this study, all doubt can be removed as the samples can vary known globulin and albumin concentrations independently of one another. The analysis of each of the proteins will be complicated by the fixed concentration of collagen with its protein like absorbance bands. The urea concentrations have an average concentration well above the normal physiological range due to the fact that urea concentrations can be hundreds of mg/dL in some individuals.

Each of the analytes in Table 4 are randomly distributed versus the concentration of all other analytes. In addition, the thirty-two corners of the cube are sampled. Finally, a sample corresponding to the center of the data space is run once per day.

The study was designed to answer the resolution specification. Representative basis set components are present in concentrations approaching that of physiological levels in serum along with collagen. Therefore, all of the major interfering absorbance bands are present. In addition, sampling is performed in diffuse reflectance mode with absorbance and scattering coefficients approximating the body. A key consideration in resolution studies is time. The signal to noise ratio, resolution and time are inter-related. As resolution is degraded, light throughput increases resulting in decreased noise levels. In addition, a reduction in noise is achieved by averaging a larger number of scans. In the noninvasive glucose measurement, the poorest resolution possible is desired to yield the greatest S/N levels per unit time. On a FT system, degraded resolution requires a shorter retardation of the movable mirror. This allows a greater number of co-added scans per spectrum. Unfortunately, collecting the entire Intra-gel study at all resolutions is not feasible. Therefore, the spectra are collected at high resolution.

An interferogram may be reprocessed using fewer points to yield spectra with degraded resolutions. Replicate spectra are averaged together to simulate the additional spectra that may have been achieved at degraded resolutions. For example, one spectrum at 4 $cm^{-1}$ resolution with 32 co-added spectra can be used per sample in the analysis of glucose. However, at 8 $cm^{-1}$ resolution, two spectra with 32 co-added scans per spectrum resolution may be averaged for each sample. Similarly, at 16 $cm^{-1}$ resolution four spectra are co-added and at 32 $cm^{-1}$ resolution eight spectra may be co-added. This experimental design accepts a priori that the spectra collected at poorer resolution should have been acquired in the same time period as at the highest resolution. This is not the case. Therefore, short term instrument drift has a systematically larger impact as the resolution is degraded.

Experimental

Sample Preparation

A 5% and 10% Intra-gel sample are prepared from a 30% Intralipid stock solution. The Intralipid stock solution is transferred via micro-pipettes to a ten dram vial. De-ionized water is then quantitatively added to the vial. The resulting solution is brought to 50±1° C. by placing into a hot water bath. While maintaining the solution at 50±1° C., the collagen is to be added to the sample. The resulting solution is to be stirred with a miniature stirrer (Micro-Mark, P/N 80975) until the collagen is completely dissolved (typically four minutes). The solution is then poured into a metal cast maintained at 0° C. in an ice bath. The cast solution is to be stirred with the miniature stirrer until it reaches 22° C. at which time the stirrer is removed. The cast sample is then left in the ice-bath for a period of fifteen minutes. This procedure is summarized in Table 5.

TABLE 5

Summary of Sample Preparation

|  | 5% Intra-gel | 10% Intra-gel |
| --- | --- | --- |
| Intralipid Stock-30% @ room temp (mL) | 3.33 | 6.66 |
| Water @ room temp (mL) Heat to 50° C. | 16.66 | 13.33 |
| Collagen (g) Stir @ 50° C. until dissolved Pour into cast at 0° C. and stir until 22° C. Slice to appropriate thickness | 1.1722 | 1.1722 |

Instrumentation

A Nicolet Magna 860 spectrometer was equipped with a custom auxiliary source, fiber optic interface and InGaAs detector. An Oriel (Stratford, Conn.) housing was used in conjunction with an L7390A Gilway 100 W tungsten-halogen lamp.

Results and Discussion

Figure 30:
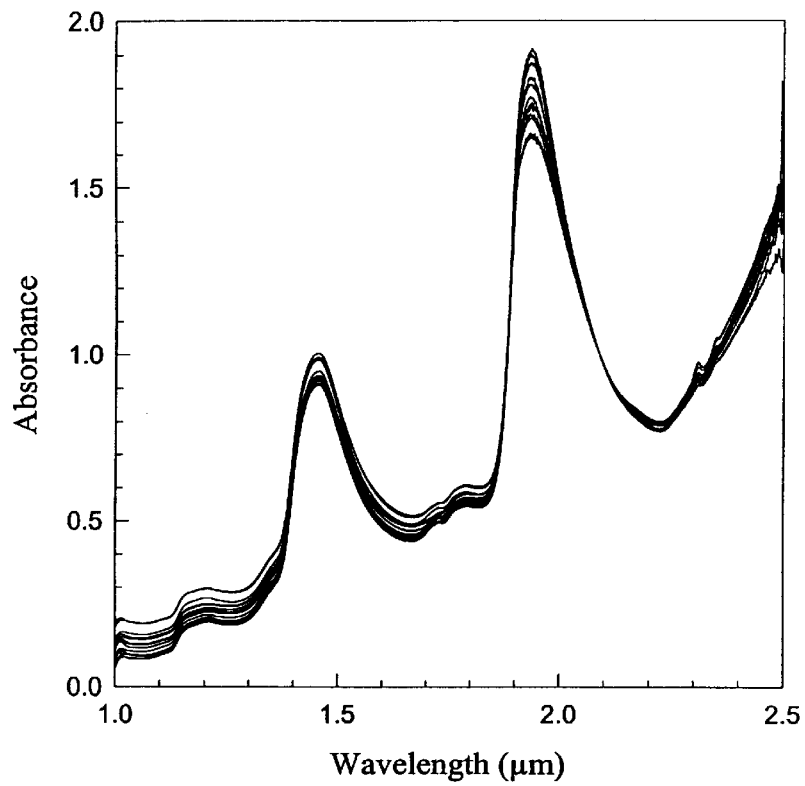
FIG. 30 shows absorbance spectra for a total of 66 Intra-gel samples after normalizing at 2100 nm.
Figure 31:
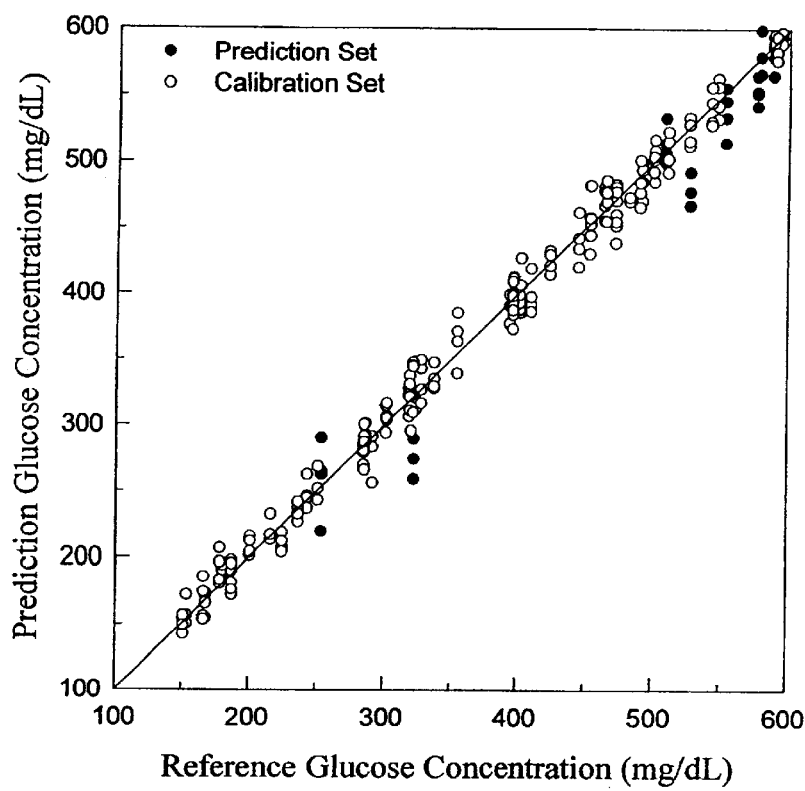
FIG. 31 shows a concentration correlation plot for the Intra-gel study with a SEC and SEP of 12.4 and 29.7 mg/dL, respectively.

A total of 66 samples were collected with sixteen replicates per sample. The absorbance spectra are presented in FIG. 30 after normalizing at 2100 nm. The samples were broken up into calibration and prediction sets and a PLS analysis was run using the 1150 to 1820 and 2100 to 2450 nm spectral regions. The resulting concentration correlation plot is presented in FIG. 31 and resulted in a SEC and SEP of 12.4 and 29.7 mg/dL, respectively. Combined with the Intra-serum results, this demonstrates the feasibility of using Intra-gel samples to model the body.

Additional Embodiments

Many other scatterers may be imbedded in the Intra-serum and crosslinked into the Intra-gel such as polystyrene beads, titanium dioxide particles ($TiO_2$) and additional scatterers known to those skilled in the art. It is also recognized that the Intra-serum and Intra-gel family of samples may be readily modified to model additional tissues and organs within the body or in animals.

Uses

Provide a physical system upon which experiments can be performed to quantitatively model tissues and organs in the body or within animals.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

What is claimed is:

1. A human tissue surrogate material, comprising:
   an emulsion comprising oil in water, and further comprising lecithin;
   wherein said lecithin comprises an emulsifier;
   wherein said emulsion models optical characteristics of skin tissue; and
   wherein said emulsion contains no glycerol therein.

2. The human tissue surrogate of claim 1, wherein said oil comprises castor oil or other oils that can form particles approximately 0.2 to 3.0 µm in size.

3. The human tissue surrogate of claim 2, wherein said castor oil has either a Gaussian or bimodal particle size distribution with peaks centered anywhere from 0.2 to 3.0 µm.

4. The human tissue surrogate of claim 2, wherein castor oil droplets are suspended in an aqueous solution with said lecithin.

5. The human tissue surrogate of claim 2, wherein particle size distribution has two widely separated peaks near 0.4 and 3.0 µm.

6. The human tissue surrogate of claim 1, wherein observed intensity in $2^{nd}$ overtone (1000 to 1450 nm), 1st overtone (1450 to 2000 nm) and combination band (2000 to 2500 nm) spectral regions of a human arm is closely modeled by said tissue surrogate.

7. The human tissue surrogate of claim 1, further comprising additional organic components.

8. The human tissue surrogate of claim 7, wherein said additional organic components comprise any of collagen, elastin, globulin, lactic acid bilirubin and electrolytes.

9. The human tissue surrogate of claim 8, wherein said electrolytes comprise any of $Na^+$, $K^+$ and $Cl^-$.

10. The human tissue surrogate of claim 1, further comprising a crosslinker.

11. The human tissue surrogate of claim 10 wherein said crosslinker comprises collagen.

12. The human tissue surrogate of claim 11, further comprising:
   albumin having a concentration of 0 to 6000 mg/dL;
   globulin having a concentration of 0 to 2500 mg/dL;
   urea having a concentration of 0 to 200 mg/dL;
   and glucose having a concentration of 0 to 800 mg/dL.

13. The human tissue surrogate of claim 12, wherein said water, oil and lecithin emulsion comprises 1.5 to 15% of said tissue surrogate.

14. The human tissue surrogate of claim 13, wherein said water, oil and lecithin emulsion comprises 2 to 4% of said tissue surrogate.

15. The human tissue surrogate of claim 11, wherein said collagen comprises gelatin.

* * * * *